United States Patent
Ginn et al.

(10) Patent No.: US 9,089,674 B2
(45) Date of Patent: *Jul. 28, 2015

(54) APPARATUS AND METHODS FOR POSITIONING A VASCULAR SHEATH

(75) Inventors: Richard S. Ginn, San Jose, CA (US); W. Martin Belef, San Jose, CA (US)

(73) Assignee: INTEGRATED VASCULAR SYSTEMS, INC., Redwood City, CA (US)

( * ) Notice: Subject to any disclaimer, the term of this patent is extended or adjusted under 35 U.S.C. 154(b) by 489 days.

This patent is subject to a terminal disclaimer.

(21) Appl. No.: 11/532,325

(22) Filed: Sep. 15, 2006

(65) Prior Publication Data

US 2007/0010853 A1    Jan. 11, 2007

Related U.S. Application Data

(63) Continuation of application No. 10/669,313, filed on Sep. 23, 2003, now Pat. No. 7,144,411, which is a continuation of application No. 09/680,837, filed on Oct. 6, 2000, now Pat. No. 6,626,918.

(51) Int. Cl.
*A61B 17/08* (2006.01)
*A61M 25/06* (2006.01)
(Continued)

(52) U.S. Cl.
CPC ........ *A61M 25/0662* (2013.01); *A61B 17/0057* (2013.01); *A61B 17/3417* (2013.01);
(Continued)

(58) Field of Classification Search
CPC ............. A61M 25/0062; A61M 25/0693; A61B 17/0057; A61B 17/3417; A61B 17/3498; A61B 2017/00672

USPC ............ 606/213, 219, 220, 185, 158; 604/275–278, 507–510

See application file for complete search history.

(56) References Cited

U.S. PATENT DOCUMENTS

| 287,046 A | 10/1883 | Norton |
| 438,400 A | 10/1890 | Brennen |

(Continued)

FOREIGN PATENT DOCUMENTS

| AU | 2003297432 | 12/2003 |
| CA | 2 339 060 | 2/2000 |

(Continued)

OTHER PUBLICATIONS

"Hand tool for forming telephone connections—comprises pliers with reciprocably driven ram crimping clip around conductors against anvil", Derwent-ACC-No. 1978-B8090A.

(Continued)

*Primary Examiner* — Alexander Orkin
(74) *Attorney, Agent, or Firm* — Workman Nydegger; Randy Shen

(57) ABSTRACT

An apparatus for positioning an introducer sheath includes a sheath having a distal end including first and second ports, the second port being located distally from the first port. An obturator is slidable within the sheath that includes a distal region that sealingly engages an interior surface of the sheath. The obturator includes first and second openings in the distal region that are alignable with the first and second ports in the sheath. A housing is slidable on the exterior of the sheath that releasably holds a closure element. The sheath may be inserted into an incision communicating with a blood vessel, the first and second ports providing backbleed indication of the depth of the insertion of the sheath into the vessel. The housing is actuated to deploy the closure element to engage and close the incision.

20 Claims, 16 Drawing Sheets

(51) Int. Cl.
*A61B 17/00* (2006.01)
*A61B 17/34* (2006.01)
*A61B 19/00* (2006.01)
*A61M 25/00* (2006.01)

(52) U.S. Cl.
CPC ... *A61B17/3498* (2013.01); *A61B 2017/00672* (2013.01); *A61B 2017/3454* (2013.01); *A61B 2019/462* (2013.01); *A61M 25/0693* (2013.01); *A61M 2025/0079* (2013.01)

(56) References Cited

U.S. PATENT DOCUMENTS

| | | | |
|---|---|---|---|
| 556,082 A | 3/1896 | Boeddinghaus |
| 1,088,393 A | 2/1914 | Backus |
| 1,242,139 A | 10/1917 | Callahan |
| 1,331,401 A | 2/1920 | Summers |
| 1,426,111 A | 8/1922 | Sacker |
| 1,480,935 A | 1/1924 | Gleason |
| 1,516,990 A | 11/1924 | Silverman |
| 1,596,004 A | 8/1926 | Becerro |
| 1,647,958 A | 11/1927 | Ciarlante |
| 1,847,347 A | 3/1932 | Maisto |
| 1,852,098 A | 4/1932 | Anderson |
| 1,880,569 A | 10/1932 | Weis |
| 2,075,508 A | 3/1937 | Davidson |
| 2,087,074 A | 7/1937 | Tucker |
| 2,108,206 A | 2/1938 | Meeker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,610,631 A | 9/1952 | Calicchio |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,348,595 A | 10/1967 | Stevens, Jr. |
| 3,357,070 A | 12/1967 | Sloan |
| 3,482,428 A | 12/1969 | Kapitanov et al. |
| 3,494,533 A | 2/1970 | Green et al. |
| 3,510,923 A | 5/1970 | Blake |
| 3,513,848 A | 5/1970 | Winston et al. |
| 3,523,351 A | 8/1970 | Filia |
| 3,525,340 A | 8/1970 | Gilbert |
| 3,586,002 A | 6/1971 | Wood |
| 3,604,425 A | 9/1971 | Le Roy |
| 3,618,447 A | 11/1971 | Goins |
| 3,664,345 A | 5/1972 | Dabbs et al. |
| 3,677,243 A | 7/1972 | Nerz |
| 3,682,180 A | 8/1972 | McFarlane |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Branstetter |
| 3,814,104 A | 6/1974 | Irnich et al. |
| 3,823,719 A | 7/1974 | Cummings |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,960,147 A | 6/1976 | Murray |
| 3,976,079 A | 8/1976 | Samuels et al. |
| 3,985,138 A | 10/1976 | Jarvik |
| 4,007,743 A | 2/1977 | Blake |
| 4,011,872 A | 3/1977 | Komiya |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,189,808 A | 2/1980 | Brown |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,267,995 A | 5/1981 | McMillan |
| 4,273,129 A | 6/1981 | Boebel |
| 4,274,415 A | 6/1981 | Kanamoto et al. |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,359,052 A | 11/1982 | Staub |
| 4,368,736 A | 1/1983 | Kaster |
| 4,387,489 A | 6/1983 | Dudek |
| 4,396,139 A | 8/1983 | Hall et al. |
| 4,400,879 A | 8/1983 | Hildreth |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| 4,501,276 A | 2/1985 | Lombardi |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,577,635 A | 3/1986 | Meredith |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,651,737 A | 3/1987 | Deniega |
| 4,664,305 A | 5/1987 | Blake, III et al. |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,693,249 A | 9/1987 | Schenck et al. |
| 4,697,312 A | 10/1987 | Freyer |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |

(56) References Cited

U.S. PATENT DOCUMENTS

| | | |
|---|---|---|
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,830,002 A | 5/1989 | Semm |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,042,707 A | 8/1991 | Taheri |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,071,430 A | 12/1991 | de Salis et al. |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,158,566 A | 10/1992 | Pianetti |
| 5,160,339 A | 11/1992 | Chen et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,251 A | 12/1992 | Bregen et al. |
| 5,171,259 A | 12/1992 | Inoue |
| 5,176,648 A | 1/1993 | Holmes et al. |
| 5,176,682 A | 1/1993 | Chow |
| 5,176,691 A | 1/1993 | Pierce |
| 5,243,857 A | 2/1993 | Velez |
| 5,192,287 A | 3/1993 | Fournier et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,193,533 A | 3/1993 | Body et al. |
| 5,197,971 A | 3/1993 | Bonutti |
| 5,203,787 A | 4/1993 | Noblitt et al. |
| 5,207,697 A | 5/1993 | Carusillo et al. |
| 5,209,756 A | 5/1993 | Seedhorm et al. |
| 5,217,024 A | 6/1993 | Dorsey et al. |
| 5,217,471 A | 6/1993 | Burkhart |
| 5,219,359 A | 6/1993 | McQuilkin et al. |
| 5,222,974 A | 6/1993 | Kensey et al. |
| 5,226,908 A | 7/1993 | Yoon |
| 5,234,449 A | 8/1993 | Bruker et al. |
| 5,236,435 A | 8/1993 | Sewell, Jr. |
| 5,236,445 A | 8/1993 | Hayhurst et al. |
| 5,237,996 A | 8/1993 | Waldman |
| 5,242,456 A | 9/1993 | Nash et al. |
| 5,242,457 A | 9/1993 | Akopov et al. |
| 5,242,459 A | 9/1993 | Buelna |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,258,015 A | 11/1993 | Li et al. |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,282,832 A | 2/1994 | Toso et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,306,280 A | 4/1994 | Bregen et al. |
| 5,309,927 A | 5/1994 | Welch |
| 5,318,542 A | 6/1994 | Hirsch et al. |
| 5,320,639 A | 6/1994 | Rudnick |
| 5,327,908 A | 7/1994 | Gerry |
| 5,330,442 A | 7/1994 | Green et al. |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,376,101 A | 12/1994 | Green et al. |
| 5,383,896 A | 1/1995 | Gershony et al. |
| 5,383,897 A | 1/1995 | Wholey |
| 5,383,905 A | 1/1995 | Golds et al. |
| RE34,866 E | 2/1995 | Kensey et al. |
| 5,391,173 A | 2/1995 | Wilk |
| 5,392,978 A | 2/1995 | Valez et al. |
| 5,395,030 A | 3/1995 | Kuramoto et al. |
| 5,403,330 A | 4/1995 | Tuason |
| 5,403,331 A | 4/1995 | Chesterfield et al. |
| 5,404,621 A | 4/1995 | Heinke |
| 5,409,499 A | 4/1995 | Yi |
| 5,411,520 A | 5/1995 | Nash et al. |

(56) References Cited

U.S. PATENT DOCUMENTS

| | | |
|---|---|---|
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,558 A | 10/1995 | Kolesa et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,474,572 A | 12/1995 | Hayhurst |
| 5,476,505 A | 12/1995 | Limon |
| 5,478,352 A | 12/1995 | Fowler |
| 5,478,353 A | 12/1995 | Yoon et al. |
| 5,478,354 A | 12/1995 | Tovey et al. |
| 5,486,195 A | 1/1996 | Myers et al. |
| 5,492,119 A | 2/1996 | Abrams |
| 5,496,332 A | 3/1996 | Sierra et al. |
| 5,497,933 A | 3/1996 | DeFonzo et al. |
| 5,501,698 A | 3/1996 | Roth et al. |
| 5,507,744 A | 4/1996 | Tay et al. |
| 5,507,755 A | 4/1996 | Gresl et al. |
| 5,510,115 A | 4/1996 | Breillatt, Jr. et al. |
| 5,514,159 A | 5/1996 | Matula et al. |
| 5,521,184 A | 5/1996 | Zimmerman |
| 5,522,840 A | 6/1996 | Krajicek |
| 5,527,322 A | 6/1996 | Klein et al. |
| 5,536,251 A | 7/1996 | Evard et al. |
| 5,536,267 A | 7/1996 | Edwards |
| 5,540,712 A | 7/1996 | Kleshinski et al. |
| 5,540,716 A | 7/1996 | Hlavacek |
| 5,543,520 A | 8/1996 | Zimmerman |
| 5,544,802 A | 8/1996 | Crainich |
| 5,547,474 A | 8/1996 | Kloeckl et al. |
| 5,560,532 A | 10/1996 | DeFonzo et al. |
| 5,562,684 A | 10/1996 | Kammerer |
| 5,571,120 A | 11/1996 | Yoon |
| 5,573,540 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,593,422 A | 1/1997 | Muijs Van der Moer et al. |
| 5,593,425 A | 1/1997 | Bonutti et al. |
| 5,601,602 A | 2/1997 | Fowler |
| 5,609,597 A | 3/1997 | Lehrer |
| 5,611,986 A | 3/1997 | Datta et al. |
| 5,613,974 A | 3/1997 | Andreas et al. |
| 5,613,975 A | 3/1997 | Christy |
| 5,618,291 A | 4/1997 | Thompson et al. |
| 5,618,306 A | 4/1997 | Roth et al. |
| 5,620,452 A | 4/1997 | Yoon |
| 5,620,461 A | 4/1997 | Muijs et al. |
| 5,626,614 A | 5/1997 | Hart |
| 5,630,824 A | 5/1997 | Hart |
| 5,634,936 A | 6/1997 | Lindon et al. |
| 5,643,318 A | 7/1997 | Tsukernik et al. |
| 5,645,553 A | 7/1997 | Kolesa et al. |
| 5,645,565 A | 7/1997 | Rudd et al. |
| 5,645,566 A | 7/1997 | Brenneman et al. |
| 5,645,567 A | 7/1997 | Crainich |
| 5,647,372 A | 7/1997 | Tovey et al. |
| 5,649,959 A | 7/1997 | Hannam et al. |
| D383,539 S | 9/1997 | Croley |
| 5,669,917 A | 9/1997 | Sauer et al. |
| 5,669,935 A | 9/1997 | Rosenman et al. |
| 5,672,174 A | 9/1997 | Gough et al. |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |
| 5,681,334 A * | 10/1997 | Evans et al. .................. 606/148 |
| 5,681,351 A | 10/1997 | Jamiolkowski et al. |
| 5,683,405 A | 11/1997 | Yacoubian et al. |
| 5,690,674 A | 11/1997 | Diaz |
| 5,693,061 A | 12/1997 | Pierce et al. |
| 5,695,504 A | 12/1997 | Gifford, III et al. |
| 5,695,505 A | 12/1997 | Yoon |
| 5,695,524 A | 12/1997 | Kelley et al. |
| 5,697,943 A | 12/1997 | Sauer et al. |
| 5,700,273 A | 12/1997 | Buelna et al. |
| 5,709,224 A | 1/1998 | Behl et al. |
| 5,709,708 A | 1/1998 | Thal |
| 5,713,899 A | 2/1998 | Marnay et al. |
| 5,715,987 A | 2/1998 | Kelley et al. |
| 5,716,375 A | 2/1998 | Fowler |
| 5,720,755 A | 2/1998 | Dakov |
| 5,720,765 A | 2/1998 | Thal |
| 5,725,498 A | 3/1998 | Janzen et al. |
| 5,725,552 A | 3/1998 | Kotula et al. |
| 5,725,554 A | 3/1998 | Simon et al. |
| 5,725,556 A | 3/1998 | Moser et al. |
| 5,728,109 A | 3/1998 | Schulze et al. |
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,133 A | 3/1998 | Kontos |
| 5,728,143 A | 3/1998 | Gough et al. |
| 5,732,872 A | 3/1998 | Bolduc et al. |
| 5,735,736 A | 4/1998 | Volk |
| 5,735,873 A | 4/1998 | MacLean |
| 5,735,875 A | 4/1998 | Bonutti et al. |
| 5,735,877 A | 4/1998 | Pagedas |
| 5,749,826 A | 5/1998 | Faulkner |
| 5,749,898 A | 5/1998 | Schulze et al. |
| 5,752,966 A | 5/1998 | Chang |
| 5,755,726 A | 5/1998 | Pratt et al. |
| 5,755,778 A | 5/1998 | Kleshinski |
| 5,759,189 A | 6/1998 | Ferragamo et al. |
| 5,766,217 A | 6/1998 | Christy |
| 5,766,246 A | 6/1998 | Mulhauser et al. |
| 5,769,862 A | 6/1998 | Kammerer et al. |
| 5,769,870 A | 6/1998 | Salahieh et al. |
| 5,776,147 A | 7/1998 | Dolendo |
| 5,776,150 A | 7/1998 | Nolan et al. |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A | 7/1998 | Cragg et al. |
| 5,782,864 A | 7/1998 | Lizardi |
| 5,795,958 A | 8/1998 | Rao et al. |
| 5,797,928 A | 8/1998 | Kogasaka |
| 5,797,929 A | 8/1998 | Andreas et al. |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |

(56) References Cited

U.S. PATENT DOCUMENTS

| | | |
|---|---|---|
| 5,810,877 A | 9/1998 | Roth et al. |
| 5,814,069 A | 9/1998 | Schulze et al. |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,221 A | 11/1998 | Stein et al. |
| 5,833,698 A | 11/1998 | Hinchliffe et al. |
| 5,843,164 A | 12/1998 | Frantzen et al. |
| 5,843,167 A | 12/1998 | Dwyer et al. |
| 5,845,657 A | 12/1998 | Carberry et al. |
| 5,846,254 A | 12/1998 | Schulze et al. |
| 5,853,421 A | 12/1998 | Leschinsky et al. |
| 5,853,422 A | 12/1998 | Huebsch et al. |
| 5,855,312 A | 1/1999 | Toledano |
| 5,855,576 A | 1/1999 | LeVeen et al. |
| 5,858,082 A | 1/1999 | Cruz et al. |
| 5,860,991 A | 1/1999 | Klein et al. |
| 5,861,003 A | 1/1999 | Latson et al. |
| 5,861,005 A | 1/1999 | Kontos |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,490 A | 2/1999 | Schulze et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,893,592 A | 4/1999 | Schulze et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,908,149 A | 6/1999 | Welch et al. |
| 5,910,155 A | 6/1999 | Ratcliff et al. |
| 5,919,207 A | 7/1999 | Taheri |
| 5,919,208 A | 7/1999 | Valenti |
| 5,922,009 A | 7/1999 | Epstein et al. |
| 5,928,231 A | 7/1999 | Klein et al. |
| 5,928,251 A | 7/1999 | Aranyi et al. |
| 5,928,260 A | 7/1999 | Chin et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,547 A | 9/1999 | Gough et al. |
| 5,951,575 A | 9/1999 | Bolduc et al. |
| 5,951,576 A | 9/1999 | Wakabayashi |
| 5,951,589 A | 9/1999 | Epstein et al. |
| 5,954,732 A | 9/1999 | Hart et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,972,023 A | 10/1999 | Tanner et al. |
| 5,976,159 A | 11/1999 | Bolduc et al. |
| 5,976,161 A | 11/1999 | Kirsch et al. |
| 5,976,174 A | 11/1999 | Ruiz |
| 5,980,517 A | 11/1999 | Gough et al. |
| 5,984,934 A | 11/1999 | Ashby et al. |
| 5,984,948 A | 11/1999 | Hasson |
| 5,984,949 A | 11/1999 | Levin |
| 5,993,466 A | 11/1999 | Yoon |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,009,877 A | 1/2000 | Edwards |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,747 A | 2/2000 | Kontos |
| 6,024,750 A | 2/2000 | Mastri |
| 6,024,756 A | 2/2000 | Huebsch et al. |
| 6,024,758 A | 2/2000 | Thal |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,744 A | 5/2000 | Edwards |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,066,160 A | 5/2000 | Colvin et al. |
| 6,068,603 A | 5/2000 | Suzuki |
| 6,071,300 A | 6/2000 | Brenneman et al. |
| 6,074,395 A | 6/2000 | Trott et al. |
| 6,074,409 A | 6/2000 | Goldfarb |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,083,242 A | 7/2000 | Cook |
| 6,086,608 A | 7/2000 | Ek et al. |
| 6,090,130 A | 7/2000 | Nash et al. |
| 6,092,561 A | 7/2000 | Schmid |
| 6,095,155 A | 8/2000 | Criscuolo |
| 6,099,553 A | 8/2000 | Hart et al. |
| 6,102,271 A | 8/2000 | Longo et al. |
| 6,106,545 A | 8/2000 | Egan |
| 6,110,184 A | 8/2000 | Weadock |
| 6,113,610 A | 9/2000 | Poncet |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |
| 6,117,159 A | 9/2000 | Huebsch et al. |
| 6,120,513 A | 9/2000 | Bailey et al. |
| 6,120,524 A | 9/2000 | Taheri |
| 6,126,675 A | 10/2000 | Schervinsky et al. |
| 6,126,677 A | 10/2000 | Ganaja et al. |
| 6,136,010 A | 10/2000 | Modesitt et al. |
| 6,143,004 A | 11/2000 | Davis |
| 6,143,017 A | 11/2000 | Thal |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,934 A | 11/2000 | Harper et al. |
| 6,152,936 A | 11/2000 | Christy et al. |
| 6,152,937 A | 11/2000 | Peterson et al. |
| 6,159,234 A | 12/2000 | Bonutti et al. |
| 6,161,263 A | 12/2000 | Anderson |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,174,324 B1 | 1/2001 | Egan et al. |
| 6,179,849 B1 | 1/2001 | Yencho et al. |
| 6,179,860 B1 | 1/2001 | Fulton, III et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,203,565 B1 | 3/2001 | Bonutti et al. |

(56) References Cited

U.S. PATENT DOCUMENTS

| | | |
|---|---|---|
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,220,248 B1 | 4/2001 | Voegele et al. |
| 6,221,084 B1 | 4/2001 | Fleenor |
| 6,221,102 B1 | 4/2001 | Baker et al. |
| 6,231,561 B1 | 5/2001 | Frazier et al. |
| 6,231,592 B1 | 5/2001 | Bonutti et al. |
| 6,238,705 B1 | 5/2001 | Liu et al. |
| 6,241,740 B1 | 6/2001 | Davis et al. |
| 6,245,079 B1 | 6/2001 | Nobles et al. |
| 6,248,124 B1 | 6/2001 | Pedros et al. |
| 6,254,615 B1 | 7/2001 | Bolduc et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,287,335 B1 | 9/2001 | Drasler et al. |
| 6,290,674 B1 | 9/2001 | Roue et al. |
| 6,296,657 B1 | 10/2001 | Brucker |
| 6,302,870 B1 | 10/2001 | Jacobsen et al. |
| 6,302,898 B1 | 10/2001 | Edwards et al. |
| 6,305,891 B1 | 10/2001 | Burlingame |
| 6,306,081 B1 | 10/2001 | Ishikawa et al. |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,397,110 B1 | 5/2002 | Kuzma |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,455,053 B1 | 9/2002 | Okada et al. |
| 6,458,130 B1 | 10/2002 | Frazier et al. |
| 6,461,364 B1 | 10/2002 | Ginn et al. |
| 6,461,366 B1 | 10/2002 | Seguin |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,498 B1 | 2/2003 | Burbank et al. |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,551,319 B2 | 4/2003 | Lieberman |
| 6,558,349 B1 | 5/2003 | Kirkman |
| 6,569,159 B1 | 5/2003 | Edwards et al. |
| 6,569,173 B1 | 5/2003 | Blatter et al. |
| 6,569,185 B2 | 5/2003 | Ungs |
| 6,572,629 B2 | 6/2003 | Kalloo et al. |
| 6,578,585 B1 | 6/2003 | Stachowski et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,596,013 B2 | 7/2003 | Yang et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,613,060 B2 | 9/2003 | Adams et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,919 B1 | 9/2003 | Swanstrom |
| 6,626,920 B2 | 9/2003 | Whayne |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,665 B2 | 1/2004 | Foley et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,051 B2 | 2/2004 | Nakada et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,736,822 B2 | 5/2004 | McClellan et al. |
| 6,743,195 B2 | 6/2004 | Zucker |
| 6,743,243 B1 | 6/2004 | Roy et al. |
| 6,743,259 B2 | 6/2004 | Ginn |
| 6,745,079 B2 | 6/2004 | King |
| 6,746,457 B2 | 6/2004 | Dana et al. |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,758,855 B2 | 7/2004 | Fulton, III et al. |
| 6,767,356 B2 | 7/2004 | Kanner et al. |
| 6,776,785 B1 | 8/2004 | Yencho et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,849,078 B2 | 2/2005 | Durgin et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 | 6/2005 | Byers, Jr. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |

(56) References Cited

U.S. PATENT DOCUMENTS

| | | |
|---|---|---|
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,391 B1 | 11/2005 | Gazzani |
| 6,969,397 B2 | 11/2005 | Ginn |
| 6,984,238 B2 | 1/2006 | Gifford, III et al. |
| 6,989,003 B2 | 1/2006 | Wing et al. |
| 6,989,016 B2 | 1/2006 | Tallarida |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,048,747 B2 | 5/2006 | Arcia et al. |
| 7,060,084 B1 | 6/2006 | Loshakove et al. |
| 7,063,661 B2 | 6/2006 | Okada |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,108,709 B2 | 9/2006 | Cummins |
| 7,108,710 B2 | 9/2006 | Anderson |
| 7,111,768 B2 | 9/2006 | Cummins et al. |
| 7,112,225 B2 | 9/2006 | Ginn |
| 7,122,002 B2 | 10/2006 | Okada |
| 7,147,646 B2 | 12/2006 | Dana et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,220,268 B2 | 5/2007 | Blatter |
| 7,229,452 B2 | 6/2007 | Kayan |
| 7,261,716 B2 | 8/2007 | Strobel et al. |
| 7,270,672 B1 | 9/2007 | Singer |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,727 B2 | 10/2008 | Cole et al. |
| 7,431,729 B2 | 10/2008 | Chanduszko |
| 7,445,596 B2 | 11/2008 | Kucklick et al. |
| 7,465,286 B2 | 12/2008 | Patterson et al. |
| 7,507,200 B2 | 3/2009 | Okada |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| 7,645,285 B2 | 1/2010 | Cosgrove et al. |
| D611,144 S | 3/2010 | Reynolds |
| 7,678,135 B2 | 3/2010 | Maahs et al. |
| 7,727,249 B2 | 6/2010 | Rahmani |
| 7,731,655 B2 | 6/2010 | Smith et al. |
| 7,749,249 B2 | 7/2010 | Gelbart et al. |
| 7,780,696 B2 | 8/2010 | Daniel et al. |
| 7,799,042 B2 | 9/2010 | Williamson, IV et al. |
| 7,819,895 B2 | 10/2010 | Ginn et al. |
| 7,875,054 B2 | 1/2011 | LaFontaine |
| 7,931,671 B2 | 4/2011 | Tenerz |
| 7,967,842 B2 | 6/2011 | Bakos |
| 8,103,327 B2 | 1/2012 | Harlev et al. |
| 8,105,352 B2 | 1/2012 | Egnelov |
| 8,226,666 B2 | 7/2012 | Zarbatany et al. |
| 8,409,228 B2 | 4/2013 | Blatter et al. |
| 2001/0007077 A1 | 7/2001 | Ginn et al. |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2001/0053909 A1 | 12/2001 | Nakada |
| 2002/0022822 A1* | 2/2002 | Cragg et al. .......... 604/500 |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0049472 A1 | 4/2002 | Coleman et al. |
| 2002/0058960 A1 | 5/2002 | Hudson et al. |
| 2002/0062104 A1* | 5/2002 | Ashby et al. ......... 604/93.01 |
| 2002/0072768 A1 | 6/2002 | Ginn |
| 2002/0077657 A1 | 6/2002 | Ginn et al. |
| 2002/0082641 A1 | 6/2002 | Ginn et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0151963 A1 | 10/2002 | Brown et al. |
| 2002/0183786 A1 | 12/2002 | Girton |
| 2002/0183787 A1 | 12/2002 | Wahr et al. |
| 2002/0188275 A1 | 12/2002 | McGuckin et al. |
| 2002/0193808 A1 | 12/2002 | Belef et al. |
| 2002/0198562 A1 | 12/2002 | Akerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0009196 A1 | 1/2003 | Peterson |
| 2003/0018358 A1 | 1/2003 | Saadat |
| 2003/0023248 A1 | 1/2003 | Parodi |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida |
| 2003/0195561 A1 | 10/2003 | Carley et al. |
| 2003/0208211 A1 | 11/2003 | Kortenbach |
| 2003/0233095 A1 | 12/2003 | Urbanski et al. |
| 2004/0009205 A1 | 1/2004 | Sawhney |
| 2004/0009289 A1 | 1/2004 | Carley et al. |
| 2004/0010285 A1 | 1/2004 | Carley et al. |
| 2004/0039414 A1 | 2/2004 | Carley et al. |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0078053 A1 | 4/2004 | Berg et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chandusko et al. |
| 2004/0093024 A1 | 5/2004 | Lousararian et al. |
| 2004/0093027 A1 | 5/2004 | Fabisiak et al. |

(56) References Cited

U.S. PATENT DOCUMENTS

| | | |
|---|---|---|
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0148818 A1 | 7/2005 | Mesallum |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0228443 A1 | 10/2005 | Yassinzadeh |
| 2005/0234508 A1 | 10/2005 | Cummins et al. |
| 2005/0245876 A1 | 11/2005 | Khosravi et al. |
| 2005/0256532 A1 | 11/2005 | Nayak et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0020270 A1 | 1/2006 | Jabba et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0089635 A1 | 4/2006 | Young et al. |
| 2006/0095029 A1 | 5/2006 | Young et al. |
| 2006/0100664 A1 | 5/2006 | Pai et al. |
| 2006/0135989 A1 | 6/2006 | Carley et al. |
| 2006/0142784 A1 | 6/2006 | Kontos |
| 2006/0144479 A1 | 7/2006 | Carley et al. |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerz |
| 2006/0229553 A1 | 10/2006 | Hammack et al. |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2006/0265012 A1 | 11/2006 | Anderson |
| 2006/0287674 A1 | 12/2006 | Ginn et al. |
| 2006/0293698 A1 | 12/2006 | Douk |
| 2007/0005093 A1 | 1/2007 | Cox |
| 2007/0010851 A1 | 1/2007 | Chanduszko et al. |
| 2007/0010854 A1 | 1/2007 | Cummins et al. |
| 2007/0021778 A1 | 1/2007 | Carly |
| 2007/0027476 A1 | 2/2007 | Harris et al. |
| 2007/0027525 A1 | 2/2007 | Ben-Muvhar |
| 2007/0049967 A1 | 3/2007 | Sibbitt, Jr. et al. |
| 2007/0049968 A1 | 3/2007 | Sibbitt, Jr. et al. |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0073337 A1 | 3/2007 | Abbott et al. |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0149996 A1 | 6/2007 | Coughlin |
| 2007/0172430 A1 | 7/2007 | Brito et al. |
| 2007/0179527 A1 | 8/2007 | Eskuri et al. |
| 2007/0185530 A1 | 8/2007 | Chin-Chen et al. |
| 2007/0203506 A1 | 8/2007 | Sibbitt, Jr. et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green, III et al. |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0004636 A1 | 1/2008 | Walberg |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0045979 A1 | 2/2008 | Ma |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0210737 A1 | 9/2008 | Ginn et al. |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0249504 A1 | 10/2008 | Lattouf et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287967 A1 | 11/2008 | Andreas et al. |
| 2008/0287988 A1 | 11/2008 | Smith et al. |
| 2008/0294001 A1 | 11/2008 | Surti |
| 2008/0300628 A1 | 12/2008 | Ellingwood |
| 2008/0312666 A1 | 12/2008 | Ellingwood et al. |
| 2008/0312686 A1 | 12/2008 | Ellingwood |
| 2008/0312740 A1 | 12/2008 | Wachter et al. |
| 2008/0319475 A1 | 12/2008 | Clark |
| 2009/0054912 A1 | 2/2009 | Heanue et al. |
| 2009/0105728 A1 | 4/2009 | Noda et al. |
| 2009/0112306 A1 | 4/2009 | Bonsignore et al. |

(56) References Cited

U.S. PATENT DOCUMENTS

| | | |
|---|---|---|
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0171388 A1 | 7/2009 | Dave et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0042144 A1 | 2/2010 | Bennett |
| 2010/0114156 A1 | 5/2010 | Mehl |
| 2010/0114159 A1 | 5/2010 | Roorda et al. |
| 2010/0130965 A1 | 5/2010 | Sibbitt, Jr. et al. |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0249828 A1 | 9/2010 | Mavani et al. |
| 2011/0066163 A1 | 3/2011 | Cho et al. |
| 2011/0082495 A1 | 4/2011 | Ruiz |
| 2011/0178548 A1 | 7/2011 | Tenerz |
| 2011/0270282 A1 | 11/2011 | Lemke |
| 2012/0035630 A1 | 2/2012 | Roorda |
| 2012/0101520 A1 | 4/2012 | Ginn et al. |
| 2012/0245603 A1 | 9/2012 | Voss |
| 2012/0245623 A1 | 9/2012 | Kariniemi et al. |
| 2012/0245626 A1 | 9/2012 | Ellingwood et al. |
| 2012/0310261 A1 | 12/2012 | Cummins et al. |
| 2013/0006274 A1 | 1/2013 | Walberg et al. |
| 2013/0338708 A1 | 12/2013 | Cummins et al. |
| 2014/0142624 A1 | 5/2014 | Pantages et al. |
| 2014/0309686 A1 | 10/2014 | Ginn et al. |
| 2014/0364900 A1 | 12/2014 | Fortson et al. |
| 2014/0364903 A1 | 12/2014 | Roorda et al. |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 197801 | 6/1967 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 95/21573 | 8/1995 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 97/28745 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/060941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/028286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |

(56) References Cited

FOREIGN PATENT DOCUMENTS

| | | |
|---|---|---|
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 60/696,069, filed Jul. 1, 2005, Pantages et al.
U.S. Appl. No. 60/843,325, filed Sep. 8, 2006, Carly.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 12/113,092, filed Apr. 30, 2008, Ginn et al.
U.S. Appl. No. 12/393,877, filed Feb. 26, 2009, Ellingwood et al.
U.S. Appl. No. 12/402,398, filed Mar. 11, 2009, Carley et al.
U.S. Appl. No. 12/403,256, filed Mar. 12, 2009, Carley et al.
U.S. Appl. No. 12/403,277, filed Mar. 12, 2009, Coleman et al.
Database WPI; Section PQ, Week 200120; Derwent Publications Ltd., London GB; AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.

J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials and Devices, Shock., Mar. 1999, p. 226, vol. 11—No. 3, Institution Northwestern University.
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
McCarthy, et al., "Tension (Stay) Suture Bridge", J. of International College of Surgeons, 34(5), pp. 613-614 (Nov. 1960).
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive. org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Stretch Comb by Scunci, retrieved via internet at www.scunci.com/productdetail by examiner on Oct. 9, 2007, publication date unavailable.
Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

(56) References Cited

OTHER PUBLICATIONS

SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.
UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
PCT Publication No. WO 00/07640, Steven J. Tallarida, "Vascular Suction Cannula, Dilator and Surgical Stapler", Feb. 17, 2000.
McCarthy, et al., "Tension (Stay) Suture Bridge", J. of International College of Surgeons, 34(5), pp. 613-614 (Nov. 1960). cited by other.
U.S. Appl. No. 12/113,851, Dec. 16, 2010, Office Action.
U.S. Appl. No. 12/114,091, Dec. 17, 2010, Office Action.
U.S. Appl. No. 12/684,470, Dec. 20, 2011, Restriction Requirement.
U.S. Appl. No. 12/684,569, Dec. 20, 2011, Restriction Requirement.
U.S. Appl. No. 11/675,462, Dec. 22, 2011, Notice of Allowance.
U.S. Appl. No. 12/608,773, Jun. 7, 2012, Office Action
U.S. Appl. No. 13/026,989, Jun. 8, 2012, Office Action.
U.S. Appl. No. 12/338,977, Jun. 19, 2013, Office Action.
U.S. Appl. No. 12/481,377, Jun. 21, 2011, Office Action.
U.S. Appl. No. 12/114,091, Jul. 7, 2011, Office Action.
U.S. Appl. No. 12/945,646, Jul. 6, 2011, Office Action.
U.S. Appl. No. 13/525,839, filed Jun. 18, 2012, Carley et al.
U.S. Appl. No. 11/427,297, Jun. 26, 2012, Notice of Allowance.
U.S. Appl. No. 11/767,818, Jul. 4, 2012, Issue Notification.
U.S. Appl. No. 12/338,977, Jul. 11, 2012, Office Action.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 61/097,072, filed Sep. 15, 2008, Sibbitt Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
U.S. Appl. No. 12/642,319, filed Dec. 18, 2009, Clark.
U.S. Appl. No. 10/006,400, Apr. 27, 2010, Notice of Allowance.
U.S. Appl. No. 10/147,774, Jun. 8, 2010, Office Action.
U.S. Appl. No. 10/264,306, Jun. 15, 2010, Office Action.
U.S. Appl. No. 10/356,214, May 13, 2010, Notice of Allowance.
U.S. Appl. No. 10/435,104, Jun. 2, 2010, Office Action.
U.S. Appl. No. 10/517,004, Apr. 23, 2010, Notice of Allowance.
U.S. Appl. No. 10/541,083, May 10, 2010, Notice of Allowance.
U.S. Appl. No. 10/616,832, May 12, 2010, Notice of Allowance.
U.S. Appl. No. 10/638,115, Apr. 2, 2010, Notice of Allowance.
U.S. Appl. No. 10/667,144, Jun. 22, 2010, Office Action.
U.S. Appl. No. 10/682,459, Apr. 28, 2010, Office Action.
U.S. Appl. No. 11/048,503, Apr. 26, 2010, Notice of Allowance.
U.S. Appl. No. 11/152,562, Mar. 31, 2010, Office Action.
U.S. Appl. No. 11/198,811, Jun. 29, 2010, Notice of Allowance.
U.S. Appl. No. 11/316,775, Apr. 16, 2008, Office Action.
U.S. Appl. No. 11/316,775, Aug. 6, 2008, Office Action.
U.S. Appl. No. 11/344,891, May 7, 2010, Office Action.
U.S. Appl. No. 11/390,586, Jul. 6, 2010, Office Action.
U.S. Appl. No. 11/396,141, May 4, 2010, Office Action.
U.S. Appl. No. 11/396,731, Jun. 29, 2010, Office Action.
U.S. Appl. No. 11/406,203, Jun. 18, 2010, Notice of Allowance.
U.S. Appl. No. 11/508,656, Dec. 9, 2009, Office Action.
U.S. Appl. No. 11/508,656, Mar. 25, 2010, Office Action.
U.S. Appl. No. 11/508,662, Dec. 28, 2009, Office Action.
U.S. Appl. No. 11/508,662, Apr. 14, 2010, Office Action.
U.S. Appl. No. 11/508,715, Jan. 6, 2010, Office Action.
U.S. Appl. No. 11/508,715, Apr. 26, 2010, Office Action.
U.S. Appl. No. 11/532,576, Apr. 23, 2010, Office Action.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/767,818, Dec. 24, 2009, Office Action.
U.S. Appl. No. 11/767,818, Mar. 22, 2010, Office Action.
U.S. Appl. No. 11/852,190, Jun. 24, 2010, Office Action.
U.S. Appl. No. 11/958,295, May 25, 2010, Office Action.
U.S. Appl. No. 11/959,334, Apr. 14, 2010, Notice of Allowance.
U.S. Appl. No. 12/106,928, May 10, 2010, Office Action.
U.S. Appl. No. 12/113,851, Apr. 27, 2010, Office Action.
U.S. Appl. No. 12/113,851, Jun. 24, 2010, Office Action.
U.S. Appl. No. 12/402,398, May 20, 2010, Office Action.
U.S. Appl. No. 12/403,256, Mar. 30, 2010, Office Action.
U.S. Appl. No. 11/390,586, Jul. 18, 2012, Issue Notification.
U.S. Appl. No. 12/608,773, Jul. 20, 2012, Office Action.
U.S. Appl. No. 12/684,569, Jul. 30, 2012, Office Action.
U.S. Appl. No. 13/039,087, Jul. 17, 2012, Office Action.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 10/006,400, Aug. 2, 2010, Notice Allowance.
U.S. Appl. No. 10/517,004, Aug. 3, 2010, Notice of Allowance.
U.S. Appl. No. 10/541,083, Aug. 17, 2010, Notice of Allowance.
U.S. Appl. No. 11/048,503, Sep. 30, 2010, Notice of Allowance.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/757,108, Nov. 25, 2009, Office Action.
U.S. Appl. No. 12/403,256, Aug. 19, 2010, Notice of Allowance.
U.S. Appl. No. 12/608,769, Aug. 22, 2012, Office Action.
U.S. Appl. No. 12/642,319, Aug. 28, 2012, Office Action.
U.S. Appl. No. 12/684,562, Aug. 21, 2012, Office Action.
U.S. Appl. No. 09/866,551, filed May 25, 2001, Ginn.
U.S. Appl. No. 10/638,115, Aug. 13, 2010, Notice of Allowance.
U.S. Appl. No. 10/787,073, Aug. 25, 2010, Notice of Allowance.
U.S. Appl. No. 11/396,731, Sep. 1, 2011, Office Action.
U.S. Appl. No. 12/548,274, Sep. 10, 2012, Office Action.
U.S. Appl. No. 12/684,470, Aug. 30, 2012, Office Action.
U.S. Appl. No. 12/684,542, Sep. 13, 2012, Office Action.
U.S. Appl. No. 13/026,989, Sep. 16, 2011, Office Action.
U.S. Appl. No. 11/508,656, Aug. 30, 2010, Office Action.
U.S. Appl. No. 11/675,462, Aug. 31, 2010, Office Action.
U.S. Appl. No. 11/958,281, Sep. 2, 2010, Office Action.
U.S. Appl. No. 12/393,877, Sep. 29, 2011, Office Action.
U.S. Appl. No. 12/402,398, Sep. 20, 2012, Office Action.
U.S. Appl. No. 12/688,065, Oct. 12, 2012, Office Action.
U.S. Appl. No. 12/848,642, Sep. 20, 2012, Office Action.
U.S. Appl. No. 12/987,792, Sep. 17, 2012, Office Action.
U.S. Appl. No. 10/616,832, Sep. 20, 2010, Notice of Allowance.
U.S. Appl. No. 10/787,073, Sep. 15, 2010, Issue Notification.
U.S. Appl. No. 11/152,562, Sep. 16, 2010, Notice of Allowance.
U.S. Appl. No. 11/427,297, Sep. 15, 2010, Office Action.

(56) References Cited

OTHER PUBLICATIONS

U.S. Appl. No. 11/767,818, Sep. 30, 2010, Office Action.
U.S. Appl. No. 12/365,397, Sep. 13, 2010, Office Action.
U.S. Appl. No. 10/356,214, Sep. 3, 2010, Notice of Allowance.
U.S. Appl. No. 10/435,104, Oct. 5, 2010, Notice of Allowance.
U.S. Appl. No. 10/682,459, Oct. 12, 2010, Office Action.
U.S. Appl. No. 11/406,203, Oct. 6, 2010, Issue Notification.
U.S. Appl. No. 11/532,576, Oct. 13, 2010, Notice of Allowance.
U.S. Appl. No. 11/958,281, Oct. 8, 2010, Office Action.
U.S. Appl. No. 12/114,031, Oct. 5, 2010, Office Action.
U.S. Appl. No. 12/403,277, Oct. 12, 2010, Office Action.
U.S. Appl. No. 11/508,715, Oct. 18, 2010, Office Action.
U.S. Appl. No. 12/114,031, May 11, 2011, Office Action.
U.S. Appl. No. 12/143,020, May 11, 2011, Office Action.
U.S. Appl. No. 13/898,202, filed May 20, 2013, Walberg et al.
U.S. Appl. No. 13/153,594, May 29, 2013, Office Action.
U.S. Appl. No. 13/791,829, May 29, 2013, Office Action.
U.S. Appl. No. 13/153,594, filed Jun. 6, 2011, Reyes et al.
U.S. Appl. No. 10/667,144, Jun. 6, 2011, Office Action.
U.S. Appl. No. 11/427,309, Jun. 7, 2013, Notice of Allowance.
U.S. Appl. No. 13/112,618, Jun. 7, 2013, Office Action.
U.S. Appl. No. 13/488,233, Jun. 5, 2013, Issue Notification.
U.S. Appl. No. 10/638,115, Dec. 22, 2010, Issue Notification.
U.S. Appl. No. 12/481,377, Jan. 3, 2012, Office Action.
U.S. Appl. No. 12/548,274, Dec. 28, 2011, Office Action.
U.S. Appl. No. 12/684,562, Dec. 28, 2011, Office Action.
U.S. Appl. No. 11/113,549, Jan. 4, 2011, Office Action.
U.S. Appl. No. 12/608,773, Jan. 7, 2013, Office Action.
U.S. Appl. No. 13/490,143, Jan. 4, 2013, Office Action.
U.S. Appl. No. 12/897,358, Jan. 12, 2012, Notice of Allowance.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/945,646, filed Nov. 12, 2010, Carley et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 10/006,400, Nov. 10, 2010, Issue Notification.
U.S. Appl. No. 10/435,104, Jan. 12, 2011, Issue Notification.
U.S. Appl. No. 12/402,398, Jan. 24, 2011, Office Action.
U.S. Appl. No. 12/945,646, Jan. 20, 2011, Office Action.
U.S. Appl. No. 12/338,977, Jan. 19, 2012, Office Action.
U.S. Appl. No. 12/684,569, Jan. 27, 2012, Office Action.
U.S. Appl. No. 11/767,818, Feb. 3, 2012, Notice of Allowance.
U.S. Appl. No. 12/684,542, Jan. 30, 2012, Office Action.
U.S. Appl. No. 12/941,809, Jan. 30, 2012, Office Action.
U.S. Appl. No. 12/966,923, Feb. 3, 2012, Notice of Allowance.
U.S. Appl. No. 12/143,020, Feb. 23, 2012, Notice of Allowance.
U.S. Appl. No. 12/548,274, Mar. 2, 2012, Office Action.
U.S. Appl. No. 12/642,319, Feb. 27, 2012, Office Action.
U.S. Appl. No. 12/113,851, Apr. 27, 2011, Office Action.
U.S. Appl. No. 12/481,377, Apr. 28, 2011, Office Action.
U.S. Appl. No. 12/961,331, Feb. 1, 2013, Office Action.
U.S. Appl. No. 13/488,233, Feb. 5, 2013, Notice of Allowance.
U.S. Appl. No. 13/039,087, filed Mar. 2, 2011, Palermo et al.
U.S. Appl. No. 11/852,190, Mar. 2, 2011, Office Action.
U.S. Appl. No. 12/122,603, Mar. 3, 2011, Office Action.
U.S. Appl. No. 11/958,281, Mar. 10, 2011, Office Action.
U.S. Appl. No. 12/402,398, Mar. 13, 2013, Notice of Allowance.
U.S. Appl. No. 13/028,041, Jan. 4, 2013, Office Action.
U.S. Appl. No. 13/028,041, Feb. 26, 2013, Office Action.
U.S. Appl. No. 11/532,576, Mar. 16, 2011, Issue Notification.
U.S. Appl. No. 11/396,731, Mar. 22, 2011, Office Action.
U.S. Appl. No. 11/427,297, Mar. 21, 2011, Office Action.
U.S. Appl. No. 12/114,031, Mar. 6, 2012, Office Action.
U.S. Appl. No. 12/684,470, Mar. 23, 2012, Office Action.
U.S. Appl. No. 12/688,065, Mar. 13, 2012, Office Action.
U.S. Appl. No. 12/897,358, Mar. 5, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 12/113,851, Mar. 29, 2012, Office Action.
U.S. Appl. No. 12/403,277, Apr. 3, 2012, Office Action.
U.S. Appl. No. 60/693,531, filed Jun. 24, 2005, Carly.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
Taber's Cyclopedic Medical Dictionary, 18th Ed. 1997, pp. 747 and 1420.
U.S. Appl. No. 10/006,400, Jan. 13, 2010, Notice of Allowance.
U.S. Appl. No. 10/147,774, Oct. 26, 2009, Office Action.
U.S. Appl. No. 10/264,306, Jan. 27, 2010, Office Action.
U.S. Appl. No. 10/356,214, Jan. 13, 2010, Notice of Allowance.
U.S. Appl. No. 10/435,104, Jan. 20, 2010, Notice of Allowance.
U.S. Appl. No. 10/517,004, Jan. 11, 2010, Notice of Allowance.
U.S. Appl. No. 10/541,083, Feb. 5, 2010, Notice of Allowance.
U.S. Appl. No. 10/616,832, Jan. 11, 2010, Notice of Allowance.
U.S. Appl. No. 10/541,083, Sep. 30, 2009, Notice of Allowance.
U.S. Appl. No. 10/638,115, Dec. 1, 2009, Notice of Allowance.
U.S. Appl. No. 10/667,144, Nov. 23, 2009, Office Action.
U.S. Appl. No. 10/682,459, Dec. 23, 2009, Office Action.
U.S. Appl. No. 10/786,444, Jan. 14, 2010, Office Action.
U.S. Appl. No. 10/787,073, Feb. 17, 2010, Notice of Allowance.
U.S. Appl. No. 10/908,721, Feb. 2, 2010, Office Action.
U.S. Appl. No. 11/048,503, Jan. 11, 2010, Notice of Allowance.
U.S. Appl. No. 11/344,891, Oct. 7, 2009, Office Action.
U.S. Appl. No. 11/455,993, Feb. 17, 2009, Office Action.
U.S. Appl. No. 11/455,993, Dec. 16, 2009, Office Action.
U.S. Appl. No. 11/532,576, Mar. 1, 2010, Restriction Requirement.
U.S. Appl. No. 11/675,462, Dec. 10, 2009, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 12/106,937, Nov. 18, 2009, Office Action.
U.S. Appl. No. 12/106,928, Oct. 5, 2009, Office Action.
U.S. Appl. No. 12/402,398, Mar. 9, 2010, Restriction Requirement.
U.S. Appl. No. 12/403,256, Dec. 16, 2009, Restriction Requirement.
U.S. Appl. No. 29/296,370, Feb. 10, 2010, Issue Notification.
U.S. Appl. No. 10/682,459, Apr. 1, 2011, Notice of Allowance.
U.S. Appl. No. 12/403,277, Mar. 31, 2011, Office Action.
U.S. Appl. No. 13/791,829, filed Mar. 8, 2013, Roorda et al.
U.S. Appl. No. 13/791,846, filed Mar. 8, 2013, Palermo.
U.S. Appl. No. 13/112,618, Mar. 29, 2013, Office Action.
U.S. Appl. No. 13/112,631, Mar. 29, 2013, Office Action.
U.S. Appl. No. 13/308,227, Apr. 10, 2013, Office Action.
U.S. Appl. No. 13/525,839, Apr. 1, 2013, Office Action.
U.S. Appl. No. 10/147,774, Apr. 6, 2011, Issue Notification.
U.S. Appl. No. 12/114,091, Apr. 5, 2012, Office Action.
U.S. Appl. No. 12/684,542, Apr. 16, 2012, Office Action.
U.S. Appl. No. 11/744,089, Apr. 15, 2013, Office Action.
U.S. Appl. No. 12/850,242, Apr. 18, 2013, Office Action.
U.S. Appl. No. 13/052,634, Feb. 8, 2013, Office Action.
U.S. Appl. No. 13/052,634, Apr. 22, 2013, Office Action.
U.S. Appl. No. 13/615,547, Apr. 12, 2013, Notice of Allowance.
U.S. Appl. No. 12/122,603, Apr. 22, 2011, Office Action.
U.S. Appl. No. 13/308,227, filed Nov. 30, 2011, Yibarren.
U.S. Appl. No. 12/688,065, Apr. 26, 2012, Office Action.
U.S. Appl. No. 11/396,141, Apr. 30, 2013, Office Action.
U.S. Appl. No. 11/852,190, Apr. 24, 2013, Office Action.
U.S. Appl. No. 12/848,642, Apr. 26, 2013, Office Action.
U.S. Appl. No. 13/490,143, Apr. 29, 2013, Notice of Allowance.
U.S. Appl. No. 11/390,586, May 3, 2012, Notice of Allowance.
U.S. Appl. No. 12/684,400, May 9, 2012, Office Action.
U.S. Appl. No. 12/897,358, May 2, 2012, Issue Notification.
U.S. Appl. No. 12/966,923, May 16, 2012, Issue Notification.
U.S. Appl. No. 11/344,891, May 15, 2013, Issue Notification.
U.S. Appl. No. 12/955,859, May 16, 2013, Office Action.
U.S. Appl. No. 13/488,233, May 15, 2013, Issue Notification.
U.S. Appl. No. 12/143,020, May 30, 2012, Issue Notification.
U.S. Appl. No. 12/393,877, May 21, 2012, Office Action.
U.S. Appl. No. 12/941,809, Jun. 1, 2012, Office Action.
U.S. Appl. No. 12/945,646, May 30, 2012, Issue Notification.
U.S. Appl. No. 12/973,204, May 30, 2012, Issue Notification.
U.S. Appl. No. 13/028,041, filed Feb. 15, 2011, Von Oepen.
U.S. Appl. No. 13/112,618, filed May 20, 2011, Gianotti et al.
U.S. Appl. No. 13/112,631, filed May 20, 2011, Voss.

(56) References Cited

OTHER PUBLICATIONS

U.S. Appl. No. 12/955,859, May 26, 2011, Office Action.
U.S. Appl. No. 11/344,891, Jun. 26, 2013, Issue Notification.
U.S. Appl. No. 12/402,398, Jun. 26, 2013, Issue Notification.
U.S. Appl. No. 13/112,631, Jun. 26, 2013, Office Action.
U.S. Appl. No. 12/135,858, Jul. 13, 2011, Office Action.
U.S. Appl. No. 10/435,104, Jul. 23, 2009, Notice of Allowance.
U.S. Appl. No. 10/669,313, Oct. 31, 2005, Office Action.
U.S. Appl. No. 11/113,549, Jul. 6, 2010, Office Action.
U.S. Appl. No. 11/959,334, Jul. 23, 2010, Notice of Allowance.
U.S. Appl. No. 12/403,277, Jul. 8, 2010, Office Action.
U.S. Appl. No. 12/955,859, Jul. 21, 2011, Office Action.
U.S. Appl. No. 11/675,462, Aug. 3, 2011, Office Action.
U.S. Appl. No. 12/114,031, Aug. 2, 2011, Office Action.
U.S. Appl. No. 10/682,459, Aug. 10, 2011, Issue Notification.
U.S. Appl. No. 11/675,462, Aug. 16, 2012, Issue Notification.
U.S. Appl. No. 11/744,089, Aug. 8, 2012, Office Action.
U.S. Appl. No. 12/481,377, Aug. 10, 2012, Notice of Allowance.
U.S. Appl. No. 12/850,242, Aug. 6, 2012, Office Action.
U.S. Appl. No. 12/955,859, Aug. 6, 2012, Office Action.
U.S. Appl. No. 13/222,899, filed Aug. 31, 2011, Carley et al.
U.S. Appl. No. 12/143,020, Aug. 31, 2011, Office Action.
U.S. Appl. No. 12/897,358, Aug. 22, 2011, Office Action.
U.S. Appl. No. 12/122,603, Sep. 23, 2011, Office Action.
U.S. Appl. No. 10/667,144, Oct. 28, 2011, Notice of Allowance.
U.S. Appl. No. 12/945,646, Oct. 26, 2011, Office Action.
U.S. Appl. No. 10/264,306, Oct. 29, 2010, Notice of Allowance.
U.S. Appl. No. 12/106,928, Oct. 25, 2010, Office Action.
U.S. Appl. No. 11/427,297, Oct. 31, 2012, Issue Notification.
U.S. Appl. No. 12/114,091, Nov. 8, 2012, Office Action.
U.S. Appl. No. 12/403,277, Nov. 5, 2012, Office Action.
U.S. Appl. No. 12/608,769, Nov. 5, 2012, Notice of Allowance.
U.S. Appl. No. 12/684,400, Oct. 16, 2012, Office Action.
U.S. Appl. No. 12/848,642, Nov. 9, 2012, Office Action.
U.S. Appl. No. 12/850,242, Oct. 17, 2012, Office Action.
U.S. Appl. No. 13/039,087, Nov. 6, 2012, Notice of Allowance.
U.S. Appl. No. 11/198,811, Oct. 20, 2010, Issue Notification.
U.S. Appl. No. 11/508,662, Oct. 26, 2010, Office Action.
U.S. Appl. No. 11/852,190, Nov. 1, 2010, Office Action.
U.S. Appl. No. 12/114,091, Oct. 27, 2010, Office Action.
U.S. Appl. No. 11/427,309, Nov. 15, 2010, Office Action.
U.S. Appl. No. 10/517,004, Nov. 23, 2010, Issue Notification.
U.S. Appl. No. 12/114,031, Nov. 22, 2010, Office Action.
U.S. Appl. No. 12/403,256, Nov. 23, 2010, Issue Notification.
U.S. Appl. No. 12/961,331, filed Dec. 6, 2010, Voss.
U.S. Appl. No. 10/147,774, Dec. 2, 2010, Notice of Allowance.
U.S. Appl. No. 10/541,083, Dec. 1, 2010, Issue Notification.
U.S. Appl. No. 11/959,334, Nov. 10, 2010, Issue Notification.
U.S. Appl. No. 12/393,877, Dec. 13, 2011, Office Action.
U.S. Appl. No. 12/941,809, Dec. 13, 2011, Restriction Requirement.
U.S. Appl. No. 12/338,977, Nov. 28, 2012, Office Action.
U.S. Appl. No. 12/961,331, Dec. 4, 2012, Office Action.
U.S. Appl. No. 13/030,922, Dec. 18, 2012, Office Action.
U.S. Appl. No. 12/955,859, Dec. 15, 2011, Office Action.
U.S. Appl. No. 12/897,358, filed Oct. 4, 2010, Carley.
U.S. Appl. No. 12/966,923, filed Dec. 13, 2010, Cummins et al.
U.S. Appl. No. 11/048,503, Dec. 8, 2010, Issue Notification.
U.S. Appl. No. 11/344,891, Jan. 22, 2013, Notice of Allowance.
U.S. Appl. No. 13/030,922, Jan. 31, 2013, Office Action.
U.S. Appl. No. 13/153,594, Jan. 29, 2013, Office Action.
U.S. Appl. No. 13/615,547, Jan. 18, 2013, Office Action.
U.S. Appl. No. 10/616,832, Jan. 26, 2011, Issue Notification.
U.S. Appl. No. 11/152,562, Jan. 26, 2011, Issue Notification.
U.S. Appl. No. 12/608,769, Feb. 10, 2012, Office Action.
U.S. Appl. No. 12/684,400, Feb. 13, 2012, Office Action.
U.S. Appl. No. 12/724,304, Feb. 10, 2012, Office Action.
U.S. Appl. No. 13/017,636, filed Jan. 31, 2011, Carley et al.
U.S. Appl. No. 13/026,989, filed Feb. 14, 2011, Cummins.
U.S. Appl. No. 10/264,306, Feb. 16, 2011, Issue Notification.
U.S. Appl. No. 11/767,818, Feb. 16, 2011, Office Action.
U.S. Appl. No. 10/667,144, Feb. 15, 2012, Issue Notification.
U.S. Appl. No. 12/135,858, Feb. 16, 2012, Office Action.
U.S. Appl. No. 12/684,562, Feb. 16, 2012, Office Action.
U.S. Appl. No. 12/945,646, Feb. 21, 2012, Notice of Allowance.
U.S. Appl. No. 13/030,922, filed Feb. 18, 2011, Cummins.
U.S. Appl. No. 10/356,214, Feb. 23, 2011, Issue Notification.
U.S. Appl. No. 14/017,039, filed Sep. 3, 2013, Ellingwood et al.
U.S. Appl. No. 14/023,428, filed Sep. 10, 2013, Ellingwood.
U.S. Appl. No. 10/786,444, Jul. 11, 2013, Notice of Allowance.
U.S. Appl. No. 10/908,721, Jul. 18, 2013, Notice of Allowance.
U.S. Appl. No. 11/396,141, Aug. 21, 2013, Office Action.
U.S. Appl. No. 11/411,925, Oct. 1, 2013, Office Action.
U.S. Appl. No. 11/744,089, Aug. 8, 2013, Notice of Allowance.
U.S. Appl. No. 12/850,242, Aug. 6, 2013, Notice of Allowance.
U.S. Appl. No. 12/955,859, Aug. 1, 2013, Notice of Allowance.
U.S. Appl. No. 12/961,331, Sep. 20, 2013, Advisory Action.
U.S. Appl. No. 13/026,989, Aug. 23, 2013, Office Action.
U.S. Appl. No. 13/028,041, Aug. 21, 2013, Notice of Allowance.
U.S. Appl. No. 13/030,922, Jul. 18, 2013, Office Action.
U.S. Appl. No. 13/153,594, Oct. 16, 2013, Notice of Allowance.
U.S. Appl. No. 13/308,227, Sep. 11, 2013, Office Action.
U.S. Appl. No. 13/525,839, Jul. 15, 2013, Notice of Allowance.
U.S. Appl. No. 13/791,829, Oct. 8, 2013, Notice of Allowance.
U.S. Appl. No. 12/106,928, Jun. 28, 2013, Office Action.
U.S. Appl. No. 12/106,937, Jun. 28, 2013, Office Action.
U.S. Appl. No. 12/941,809, Jul. 3, 2013, Office Action.
U.S. Appl. No. 12/961,331, Jul. 3, 2013, Office Action.
U.S. Appl. No. 11/396,141, Nov. 4, 2013, Notice of Allowance.
U.S. Appl. No. 11/744,089, Nov. 20, 2013, Issue Notification.
U.S. Appl. No. 11/852,190, Nov. 26, 2013, Office Action.
U.S. Appl. No. 12/122,603, Nov. 20, 2013, Office Action.
U.S. Appl. No. 12/688,065, Oct. 18, 2013, Office Action.
U.S. Appl. No. 12/850,242, Nov. 20, 2013, Issue Notification.
U.S. Appl. No. 12/941,809, Nov. 8, 2013, Office Action.
U.S. Appl. No. 12/955,859, Nov. 13, 2013, Issue Notification.
U.S. Appl. No. 13/052,634, Nov. 8, 2013, Office Action.
U.S. Appl. No. 13/112,618, Nov. 20, 2013, Office Action.
U.S. Appl. No. 14/246,926, filed Apr. 7, 2014, Carley et al.
U.S. Appl. No. 14/246,973, filed Apr. 1, 2014, Carley et al.
Turn—macmillandictionary.com/dictionary.american/turn.
Turn—Merriam-webster.com/dictionary/turn.
U.S. Appl. No. 11/113,549, Mar. 14, 2014, Notice of Allowance.
U.S. Appl. No. 11/411,925, Feb. 5, 2014, Notice of Allowance.
U.S. Appl. No. 11/455,993, Jan. 29, 2014, Office Action.
U.S. Appl. No. 11/674,930, Apr. 3, 2014, Notice of Allowance.
U.S. Appl. No. 11/852,190, Feb. 12, 2014, Notice of Allowance.
U.S. Appl. No. 12/106,928, Dec. 2, 2013, Office Action.
U.S. Appl. No. 12/106,928, Mar. 25, 2014, Advisory Action.
U.S. Appl. No. 12/106,937, Jan. 22, 2014, Office Action.
U.S. Appl. No. 12/113,851, Mar. 17, 2014, Office Action.
U.S. Appl. No. 12/114,031, Mar. 10, 2014, Office Action.
U.S. Appl. No. 12/403,277, Jan. 27, 2014, Office Action.
U.S. Appl. No. 12/642,319, Dec. 16, 2013, Office Action.
U.S. Appl. No. 12/684,569, Apr. 23, 2014, Office Action.
U.S. Appl. No. 12/688,065, Apr. 8, 2014, Office Action.
U.S. Appl. No. 12/848,642, Feb. 3, 2014, Notice of Allowance.
U.S. Appl. No. 12/941,809, Feb. 3, 2014, Notice of Allowance.
U.S. Appl. No. 12/950,628, Apr. 25, 2014, Notice of Allowance.
U.S. Appl. No. 12/961,331, Apr. 25, 2014, Notice of Allowance.
U.S. Appl. No. 12/987,792, Jan. 21, 2014, Office Action.
U.S. Appl. No. 13/030,922, Jan. 8, 2014, Notice of Allowance.
U.S. Appl. No. 13/030,922, Apr. 30, 2014, Issue Notification.
U.S. Appl. No. 13/112,631, Dec. 2, 2013, Office Action.
U.S. Appl. No. 13/222,899, Jan. 10, 2014, Office Action.
U.S. Appl. No. 13/898,202, Jan. 3, 2014, Office Action.
U.S. Appl. No. 14/539,830, filed Nov. 12, 2014, Clark.
U.S. Appl. No. 14/562,467, filed Dec. 5, 2014, Ellingwood et al.
U.S. Appl. No. 11/455,993, Aug. 11, 2014, Notice of Allowance.
U.S. Appl. No. 11/455,993, Dec. 17, 2014, Issue Notification.
U.S. Appl. No. 11/958,295, Jun. 13, 2014, Notice of Allowance.
U.S. Appl. No. 12/106,928, Oct. 3, 2014, Notice of Allowance.
U.S. Appl. No. 12/113,851, Aug. 21, 2014, Office Action.
U.S. Appl. No. 12/122,603, Apr. 30, 2014, Office Action.

(56) References Cited

OTHER PUBLICATIONS

U.S. Appl. No. 12/393,877, Aug. 4, 2014, Notice of Allowance.
U.S. Appl. No. 12/403,277, Aug. 15, 2014, Office Action.
U.S. Appl. No. 12/548,274, Aug. 14, 2014, Office Action.
U.S. Appl. No. 12/608,773, Jul. 17, 2014, Office Action.
U.S. Appl. No. 12/642,319, May 27, 2014, Notice of Allowance.
U.S. Appl. No. 12/642,319, Sep. 24, 2014, Issue Notification.
U.S. Appl. No. 12/684,470, Jun. 4, 2014, Office Action.
U.S. Appl. No. 12/684,470, Nov. 14, 2014, Office Action.
U.S. Appl. No. 12/684,542, Jun. 18, 2014, Office Action.
U.S. Appl. No. 12/684,542, Dec. 1, 2014, Office Action.
U.S. Appl. No. 12/684,562, Sep. 10, 2014, Office Action.
U.S. Appl. No. 12/987,792, Jun. 11, 2014, Office Action.
U.S. Appl. No. 12/987,792, Aug. 25, 2014, Notice of Allowance.
U.S. Appl. No. 12/987,792, Dec. 17, 2014, Issue Notification.
U.S. Appl. No. 13/112,618, Dec. 15, 2014, Office Action.
U.S. Appl. No. 13/112,631, Nov. 20, 2014, Office Action.
U.S. Appl. No. 13/222,899, Jul. 31, 2014, Office Action.
U.S. Appl. No. 13/898,202, Aug. 21, 2014, Office Action.
U.S. Appl. No. 12/106,937 Mar. 5, 2015, Notice of Allowance.
U.S. Appl. No. 12/113,851 Feb. 20, 2015, Notice of Allowance.
U.S. Appl. No. 12/114,091 Feb. 12, 2015, Office Action.
U.S. Appl. No. 12/684,562 Feb. 17, 2015, Notice of Allowance.
U.S. Appl. No. 13/898,202 Feb. 10, 2015, Notice of Allowance.
U.S. Appl. No. 14/017,039 Jan. 23, 2015, Office Action.

* cited by examiner

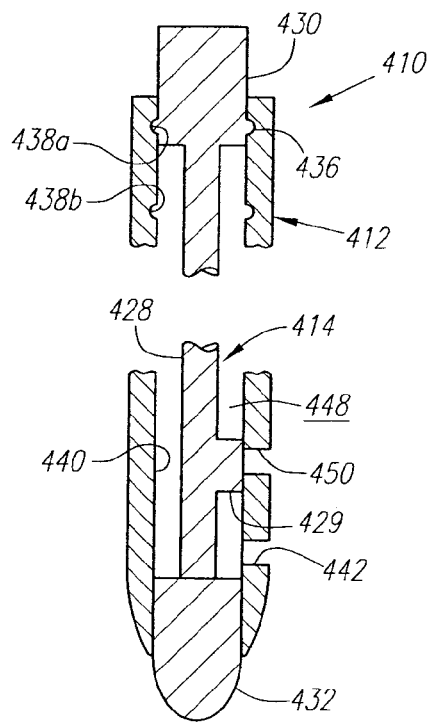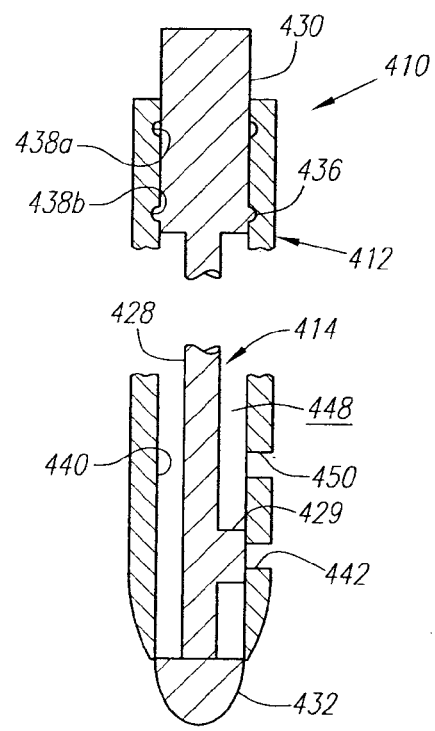
FIG. 15A   FIG. 15B
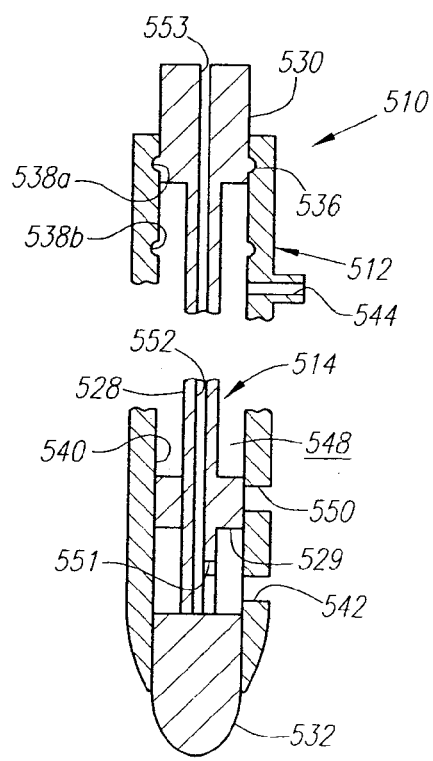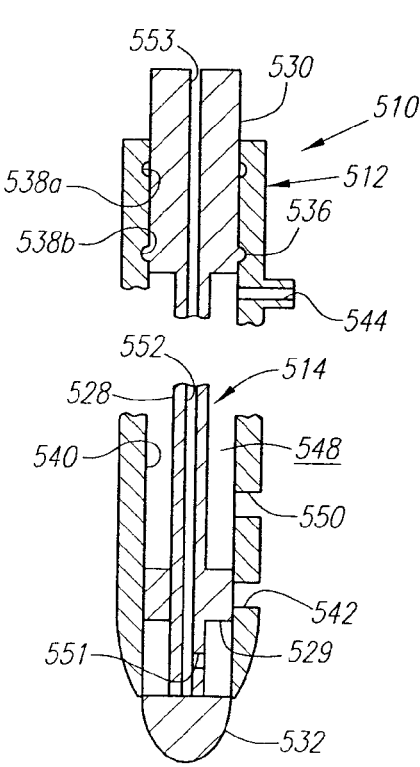
FIG. 16A   FIG. 16B

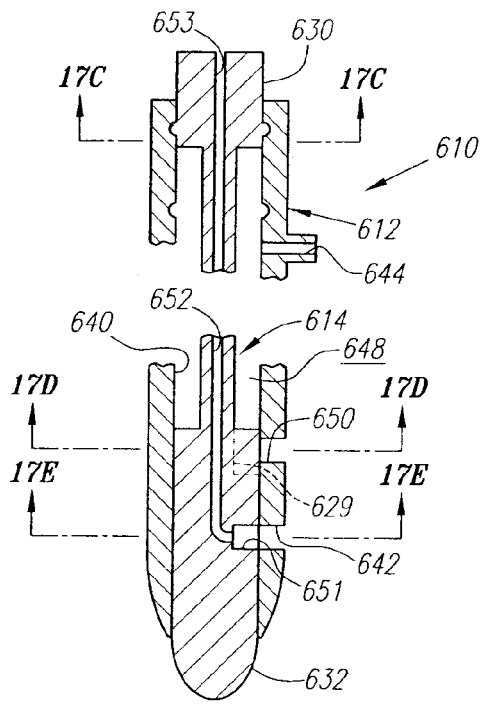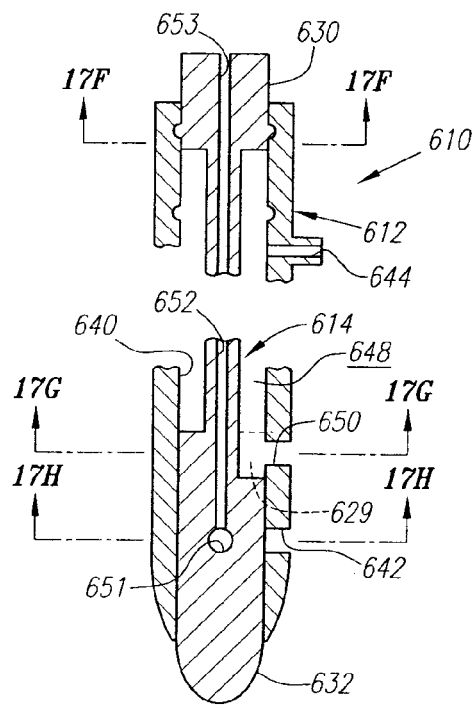
FIG. 17A    FIG. 17B
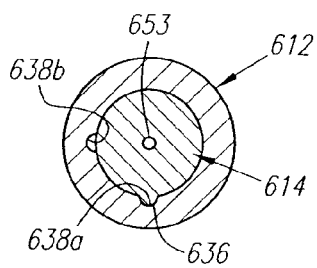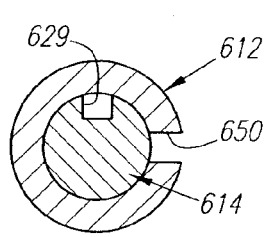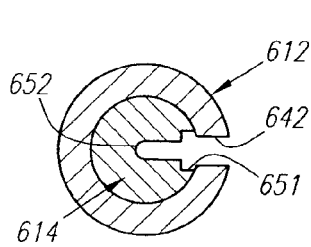
FIG. 17C    FIG. 17D    FIG. 17E
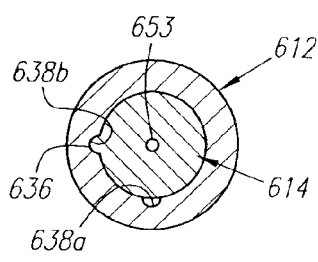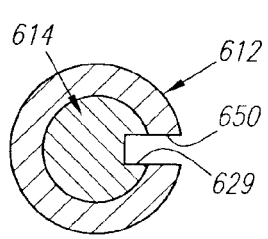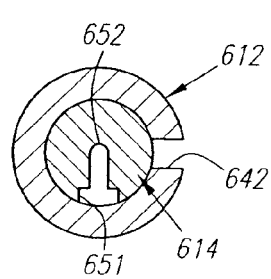
FIG. 17F    FIG. 17G    FIG. 17H

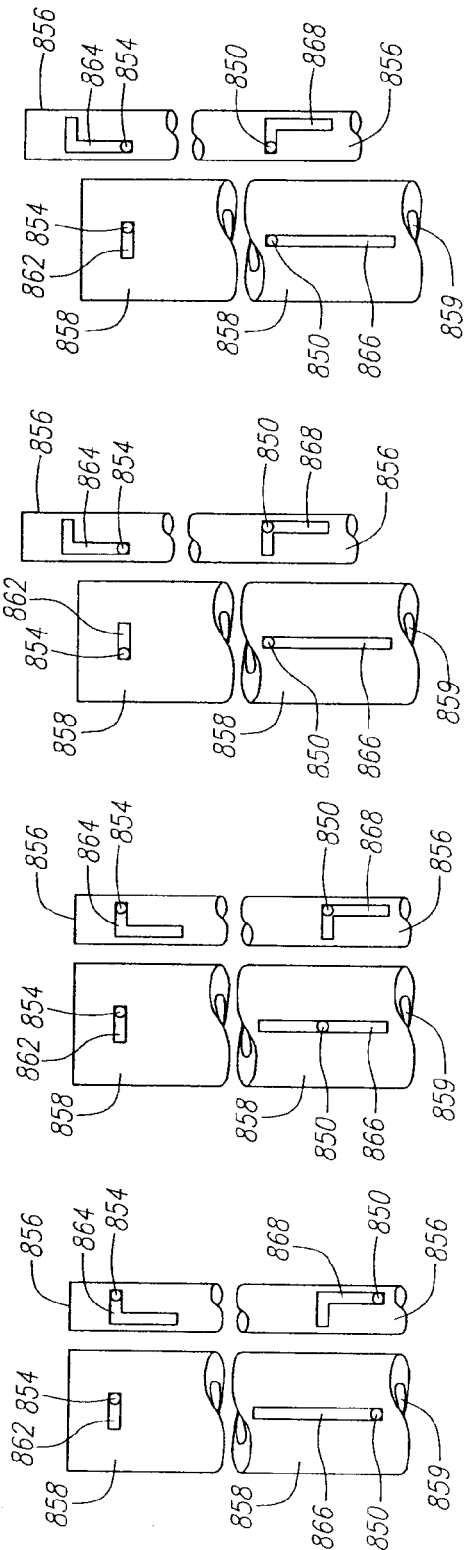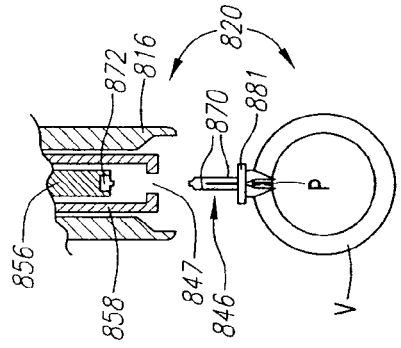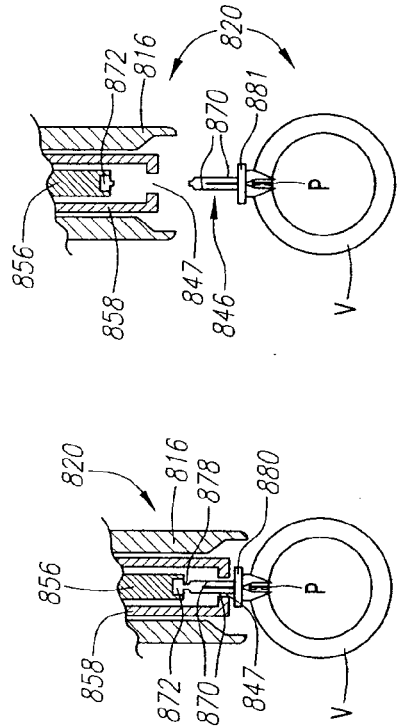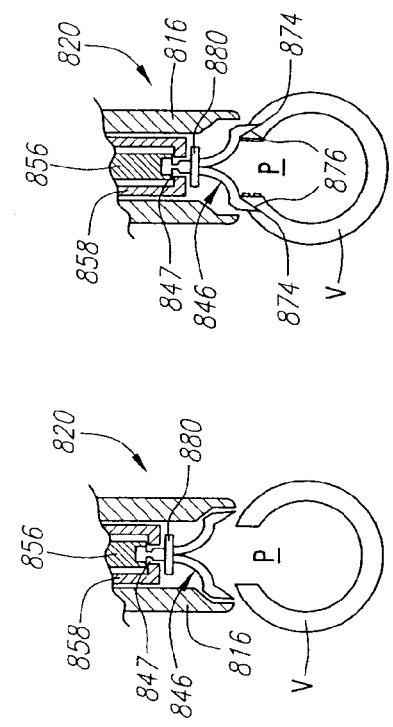

APPARATUS AND METHODS FOR POSITIONING A VASCULAR SHEATH

CROSS-REFERENCE TO RELATED APPLICATIONS

This application is a continuation of U.S. patent application Ser. No. 10/669,313, now U.S. Pat. No. 7,144,411, filed Sep. 23, 2003, and entitled "APPARATUS AND METHODS FOR POSITIONING A VASCULAR SHEATH", which is a continuation of U.S. patent application Ser. No. 09/680,837, now U.S. Pat. No. 6,626,918, filed on Oct. 6, 2000, and entitled "APPARATUS AND METHODS FOR POSITIONING A VASCULAR SHEATH", the priority of these prior applications is expressly claimed, and the disclosures of the prior applications are hereby incorporated by reference in its entirety.

BACKGROUND OF THE INVENTION

1. The Field of the Invention

The present invention relates generally to apparatus and methods for closing and/or sealing openings into body lumens, and more particularly to apparatus and methods for delivering a vascular closure element for closing an iatrogenic puncture in a blood vessel formed during a diagnostic or therapeutic procedure.

2. The Relevant Technology

Catheterization and interventional procedures, such as angioplasty or stenting, generally are performed by inserting a hollow needle through a patient's skin and muscle tissue into the vascular system. A guide wire may then be passed through the needle lumen into the patient's blood vessel accessed by the needle. The needle may be removed, and an introducer sheath may be advanced over the guide wire into the vessel. A catheter may then be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the catheter and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

To facilitate positioning devices that are percutaneously inserted into a blood vessel, "backbleed" indicators have been suggested. For example, U.S. Pat. No. 4,317,445, issued to Robinson, discloses a flashback chamber on a first end of a cannula that communicates with a port on a second end. The second end is percutaneously introduced into a patient until the port enters the vessel, whereupon blood, under normal blood pressure, may advance along the cannula and enter the flashback chamber, thereby providing a visual indication that the vessel has been entered. This reference, however, does not discuss vascular wound closure, but is merely directed to an introducer device. In contrast, U.S. Pat. No. 5,676,974, issued to Kensey et al., discloses a back bleed lumen intended to facilitate positioning of a biodegradable plug within a puncture site. This device, however, requires that an anchor of the plug be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel. The loop may also provide a support for facilitating the deployment and deflection of a surgical clip against the vessel wall. Such a device, however, may risk engagement between the loop and the surgical clip, thereby preventing the loop from being withdrawn from the vessel.

Accordingly, apparatus and methods for vascular puncture closure that are simpler to manufacture and/or use, or that overcome the disadvantages of known devices would be considered useful.

BRIEF SUMMARY OF THE INVENTION

The present invention is directed to apparatus and methods for providing access into a blood vessel or other body lumen from an incision or puncture, and/or for delivering a closure element for closing the incision.

In accordance with one aspect of the present invention, an apparatus is provided that includes a sheath having proximal and distal ends, the distal end having a size and shape for insertion into a body lumen. The distal end includes first and second ports therein, the second port being disposed at a more distal location than the first port. An obturator is disposed within the sheath, the obturator including a distal region having a size for sealingly engaging an interior surface of the sheath. The obturator includes first and second openings in the distal region, the first and second openings being alignable with the first and second ports in the sheath. First and second lumens extend distally from the proximal end of at least one of the sheath and the obturator, the first and second lumens communicating with the first and second openings, respectively. One or more of the lumens may be located within the wall of one of the sheath or obturator, or may be defined by a region between the sheath and obturator.

In addition, the apparatus may include a closure element slidably disposed on an exterior of the sheath, the closure element configured for engaging tissue adjacent an opening into a body lumen for closing the opening. Preferably, a housing is slidably disposed on the exterior of the sheath, the housing configured for releasably holding the closure element. The housing may be actuable from a proximal end of the sheath for advancing the closure element distally during deployment of the closure element.

In a preferred embodiment, the first and second ports are axially aligned with one another. A marker may then be provided on the proximal end of the tubular sheath, the marker having a predetermined peripheral orientation about the sheath for identifying the peripheral location of the first and second ports.

During use, the obturator may be inserted into the sheath, and the first and second ports may be aligned with the first and second openings when the obturator is fully inserted into the sheath. The obturator and the sheath may include cooperating detents for securing the obturator axially with respect to the sheath when the obturator is fully inserted into the sheath. Alternatively, the first opening may be aligned with the first port when the obturator is inserted a first distance into the sheath, and the second opening may be aligned with the second port when the obturator is inserted a second distance into the sheath.

In one embodiment, the first and second lumens may extend within the obturator between its proximal end and the first and second openings, respectively. Alternatively, the second lumen may extend axially through the obturator, and the first lumen may be defined by an annular lumen between the obturator and the sheath.

In accordance with another aspect of the present invention, an apparatus is provided for delivering a vascular closure element into engagement with tissue adjacent an opening into a body lumen. The apparatus includes a sheath having proximal and distal ends and an exterior surface. The sheath includes an interior surface defining a first lumen extending between the proximal and distal ends, and one or more ports in the distal end communicating with the first lumen. A housing is slidably disposed on the exterior of the sheath, the housing being configured for releasably holding a closure element. The housing is actuable from a proximal end of the sheath for advancing the closure element distally during deployment of the closure element.

An obturator is insertable into the first lumen of the sheath, the obturator including a distal region configured for sealingly engaging the interior surface of the sheath, thereby defining an annular region between the obturator and the sheath proximal to the distal region. The annular region may communicate with the one or more ports when the obturator is fully inserted into the sheath. A backbleed port may be provided on the proximal end of the sheath, the backbleed port communicating with the first lumen.

In accordance with yet another aspect of the present invention, an apparatus is provided for introduction into an opening in a wall of a body lumen. The apparatus includes a sheath having proximal and distal ends, the distal end having a size and shape for insertion into a body lumen. The distal end of the sheath includes first and second ports therein, the second port being disposed at a more distal location than the first port. The sheath may include a clip housing, a peripheral marker or other features, similar to the embodiments described above.

An obturator is disposed within the sheath, the obturator including a distal region having a size for sealingly engaging an inner surface of the sheath. The obturator is movable with respect to the sheath for selectively opening and closing the first and second side ports to permit fluid flow therethrough to the proximal end of the sheath. In one embodiment, the obturator at least partially defines a first lumen extending from the proximal end of the sheath towards the distal region of the obturator. The obturator preferably includes a region for selectively sealing the first and second ports in the sheath, whereby only one of the first and second ports communicates with the first lumen.

Preferably, the first lumen is defined between the obturator and the inner surface of the sheath. The obturator may include a second lumen therein having an inlet proximal to the distal region of the obturator and a piston for sealingly engaging the inner surface of the sheath. The piston may be located proximal to the inlet, whereby the second lumen communicates with the second side port when the obturator is disposed at a first position, and the first lumen communicates with the first side port when the obturator is disposed at a second position. The obturator may movable axially or rotated with respect to the sheath between the first and second positions.

Other objects and features of the present invention will become apparent from consideration of the following description taken in conjunction with the accompanying drawings.

BRIEF DESCRIPTION OF THE DRAWINGS

FIGS. 15A and 15B are cross-sectional views of a vascular sheath and obturator, showing first and second side ports in the sheath being selectively opened, respectively.

FIGS. 16A and 16B are cross-sectional views of an alternative embodiment of a vascular sheath and obturator, showing first and second side ports in the sheath being selectively opened, respectively.

FIGS. 17A and 17B are cross-sectional views of yet another alternative embodiment of a vascular sheath and obturator, showing first and second side ports in the sheath being selectively opened, respectively.

FIGS. 17C through 17H are cross-sectional views of the vascular sheath and obturator of FIGS. 17A and 17B.

FIGS. 21A-21B through 24A-24B are side-sectional views of the closure component in use at a vascular puncture site.

DETAILED DESCRIPTION OF THE PREFERRED EMBODIMENTS

Figure 1:
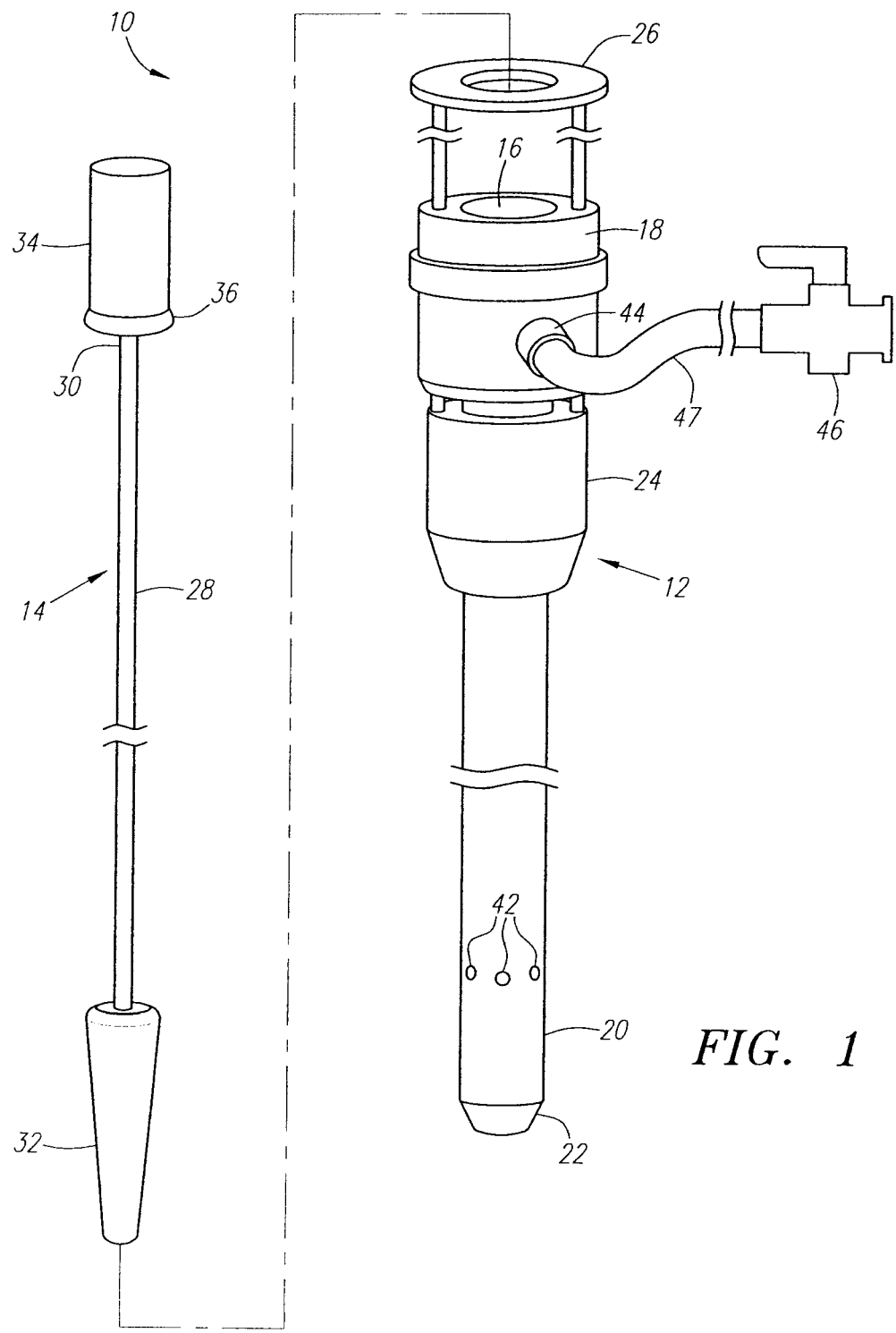
FIG. 1 is a side view of a first preferred embodiment of a vascular sheath and obturator, including a clip delivery device, in accordance with the present invention.

Turning now to the drawings, FIGS. 1-5 show a first preferred embodiment of an apparatus 10 for providing access into a blood vessel 90 or other body lumen from an incision or puncture 92 and/or for delivering a closure element (not shown) for closing the incision 92. Generally, the apparatus 10 includes a vascular sheath 12 and an obturator 14. The sheath 12 is a substantially flexible or semi-rigid tubular body including a lumen 16 extending between its proximal and distal ends 18, 20. The distal end 20 has a size and shape to facilitate insertion into a blood vessel, e.g., having a tapered tip 22 for facilitating substantially atraumatic introduction through the incision 92 and partial insertion into the vessel 90. The lumen 16 has a size to accommodate insertion of endoluminal devices therethrough, such as a catheter, guidewire, and the like (not shown).

A housing 24 is slidably disposed on an exterior of the sheath 12, the housing 24 configured for releasably holding a closure element (not shown). In a preferred embodiment, the closure element is an annular-shaped clip (not shown), including one or more barbs for engaging the tissue around the incision 92 adjacent to the wall 98 of the vessel 90. Preferably, the clip is configured for drawing the tissue around the incision 92 at the wall 98 of the vessel 90 substantially closed and/or for enhancing hemostasis within the incision 92.

The housing 24 is actuable from the proximal end 18 of the sheath 12, for example, by handle 26, for advancing the closure element distally during deployment, as described further below. Exemplary embodiments of a housing and closure element for use with an apparatus in accordance with the present invention are disclosed in co-pending application Ser. No. 09/478,179, filed Jan. 5, 2000, now U.S. Pat. No. 6,197,042, Ser. No. 09/546,998, filed Apr. 11, 2000, now U.S. Pat. No. 6,461,364, and Ser. No. 09/610,238, filed Jul. 5, 2000, now U.S. Pat. No. 6,391,048, the disclosures of which are expressly incorporated herein by reference.

The obturator 14 is a substantially flexible, or semi-rigid elongate body 28 having a proximal end 30 and an enlarged distal end 32. A handle 34 is provided on the proximal end 28 that includes an annular ridge 36 or other detent thereon that may engage a complementary-shaped pocket 38 or other cooperating detent in the sheath 12 for substantially securing the obturator 14 when it is disposed within the sheath 12, as described further below. The sheath 12 also preferably includes a seal (not shown), such as a hemostatic valve, within the lumen 16 at or near the proximal end 18 that provides a fluid-tight seal, yet accommodates insertion of devices, such as the obturator 14, into the lumen 16 without fluid passing proximally from the sheath 12.

The distal end 32 of the obturator 14 has a configuration for slidably, but sealably engaging an inner wall 40 of the sheath 12. The distal end 32 of the obturator 14 may also be substantially soft and/or flexible, possibly including a pigtail (not shown), to facilitate atraumatic advancement into a blood vessel. Alternatively, the distal end 32 of the obturator 14 may be expandable from a contracted configuration for facilitating insertion into the sheath 12 to an enlarged configuration for sealingly engaging the inner wall 40 of the sheath 12. For example, the distal end of the obturator 14 may be an inflatable balloon (not shown), and the obturator 14 may include an inflation lumen (also not shown) communicating from the proximal end 30 to an interior of the balloon for introducing fluid, such as saline, into the balloon to expand it into engagement with the inner wall 40 of the sheath 12.

Figure 2:
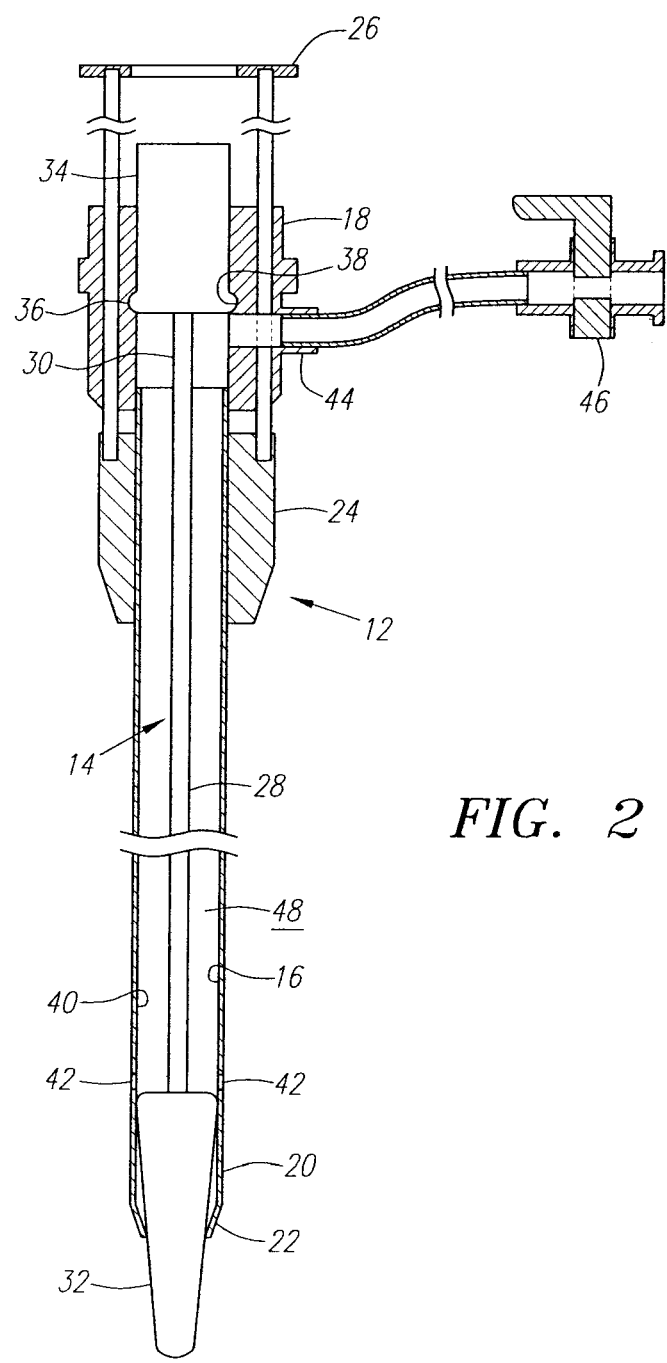
FIG. 2 is a cross-sectional view of the obturator and vascular sheath of FIG. 1, with the obturator fully inserted into the vascular sheath.

The sheath 12 includes one or more, and preferably a plurality of, distal side ports 42 at or near the distal end 20 that communicate with the lumen 16. The distal side ports 42 may be disposed circumferentially about a predetermined location with respect to the housing 24, as described further below. The sheath 12 also preferably includes a proximal side port 44 at or near the proximal end 18 that also communicates with the lumen 16, and also communicates with flush port 46, or other valve or backbleed indicator (not shown). As best seen in FIG. 2, when the obturator 14 is fully inserted into the lumen 16, the cooperating ridge and pocket 36, 38 engage one another to prevent inadvertent axial movement of the obturator 14 with respect to the sheath 12. In addition, the obturator 14 and sheath 12 together define an annular region 48 that communicates with both the distal and proximal side ports 42, 44 in the sheath 12.

Figure 3:
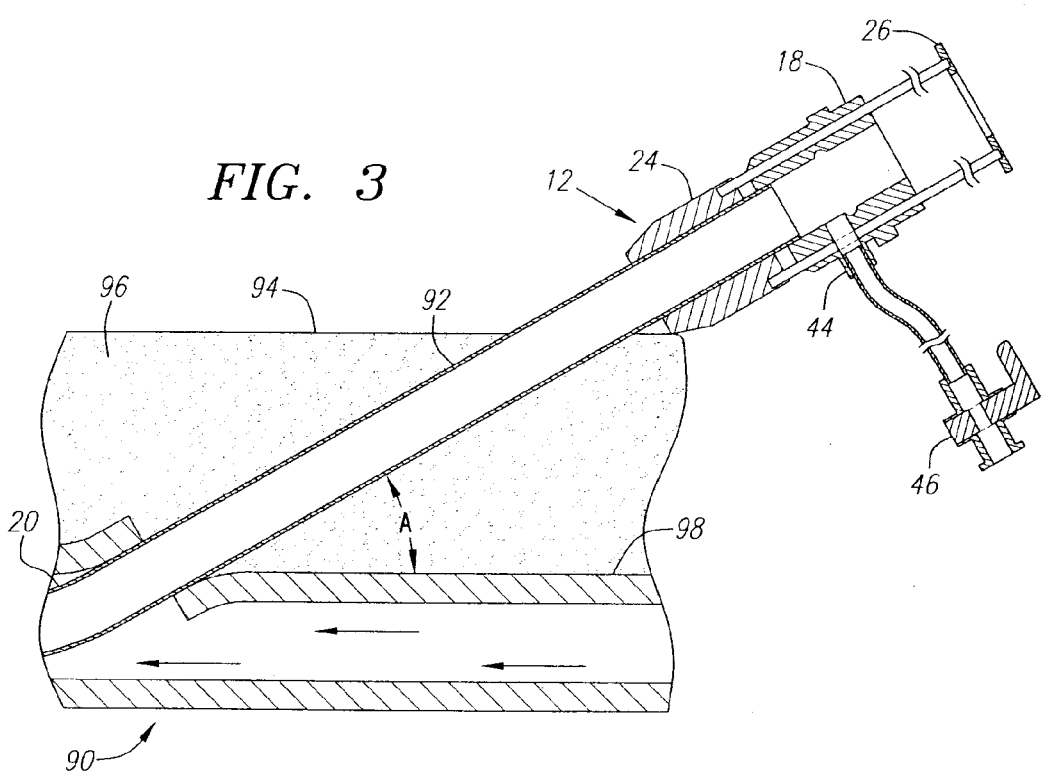
FIG. 3 is a cross-sectional view of the vascular sheath of FIG. 1 inserted through an incision into a blood vessel.

As best seen in FIG. 3, the sheath 12 may be inserted or otherwise positioned within a blood vessel 90, i.e., through an incision, puncture, or other opening 92 that extends from a patient's skin 94 through any intervening tissue 96, and a wall 98 of the vessel 90. The sheath 12 may be advanced over a guidewire or other rail (not shown) previously positioned through the incision 92 into the blood vessel 90 using a conventional procedure. Preferably, the blood vessel 90 is a peripheral vessel, such as a femoral or carotid artery, although other body lumens may be accessed using the sheath 12, as will be appreciated by those skilled in the art.

The incision 92, and consequently the sheath 12, are preferably oriented at a substantially acute angle "A" with respect to the vessel 90, thereby facilitating introduction of devices through the lumen 16 of the sheath 12 into the vessel 90 with minimal risk of damage to the vessel 90. One or more devices, such as a guide wire, a catheter, and the like may be inserted through the sheath 12 and advanced to a desired location within the patient's body. For example, the devices may be used to perform a therapeutic or diagnostic procedure, such as angioplasty, atherectomy, stent implantation, and the like, within the patient's vasculature.

Figure 4:
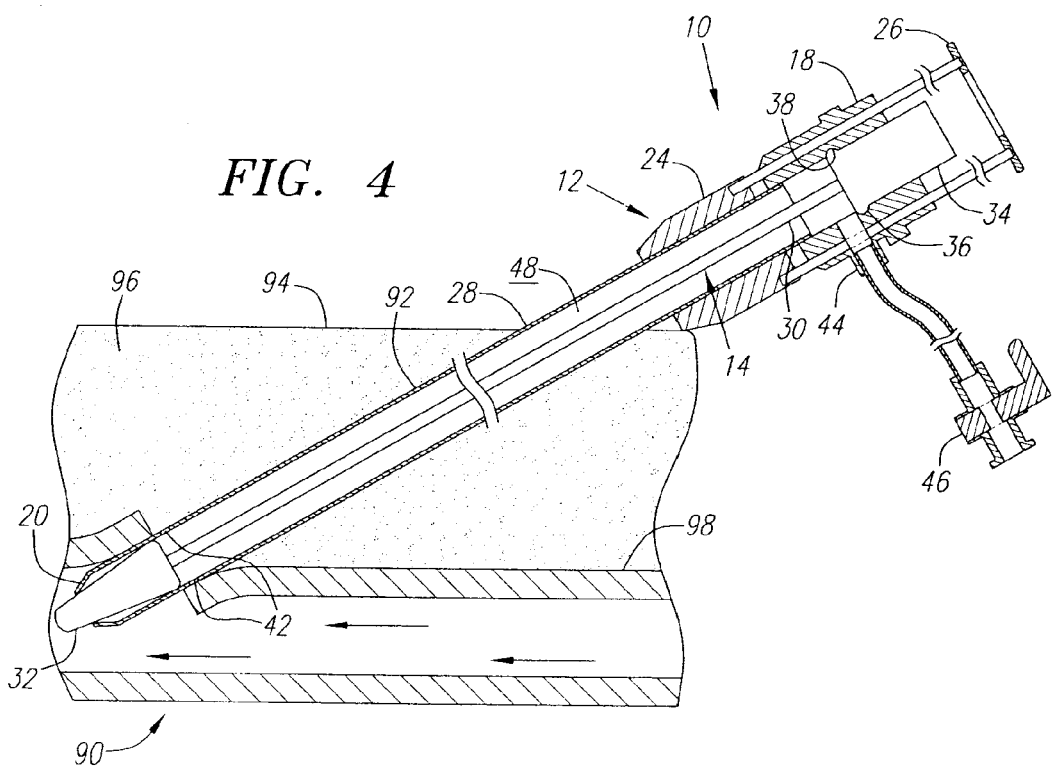
FIG. 4 is a cross-sectional view of the vascular sheath of FIG. 3 with the obturator of FIG. 1 fully inserted therein, showing side ports in the vascular sheath being disposed outside the blood vessel.

After the procedure is complete, the device(s) may be removed from the sheath 12, and the obturator 14 inserted through the hemostatic valve (not shown) into the lumen 16, e.g., until the distal end 32 extends beyond the distal end 20 of the sheath 12 and/or the cooperating detents 36, 38 are engaged, as shown in FIG. 4. Preferably, when the obturator 14 is fully inserted into the sheath 12, the distal side ports 42 communicate with the annular region 48. The sheath 12 and obturator 14 may then be moved in conjunction with one another, and preferably are together partially withdrawn from the vessel 90, as shown in FIG. 4. Preferably, the sheath 12 is positioned such that the distal side ports 42 are adjacent to and not within the vessel 90. Fluid, such as saline, may be directed into the flush port 46 to flush blood or other visible body fluid from the proximal side port 44.

Figure 5:
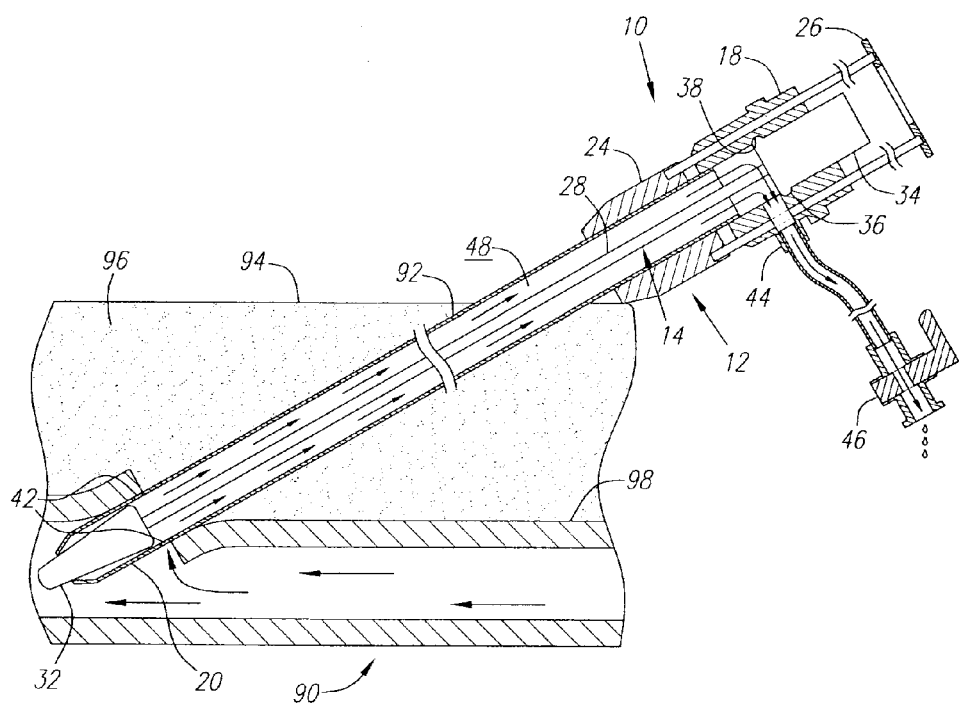
FIG. 5 is a cross-sectional view of the vascular sheath and obturator of FIG. 4 with the sheath advanced such that the side ports are disposed inside the blood vessel.
Figure 6:
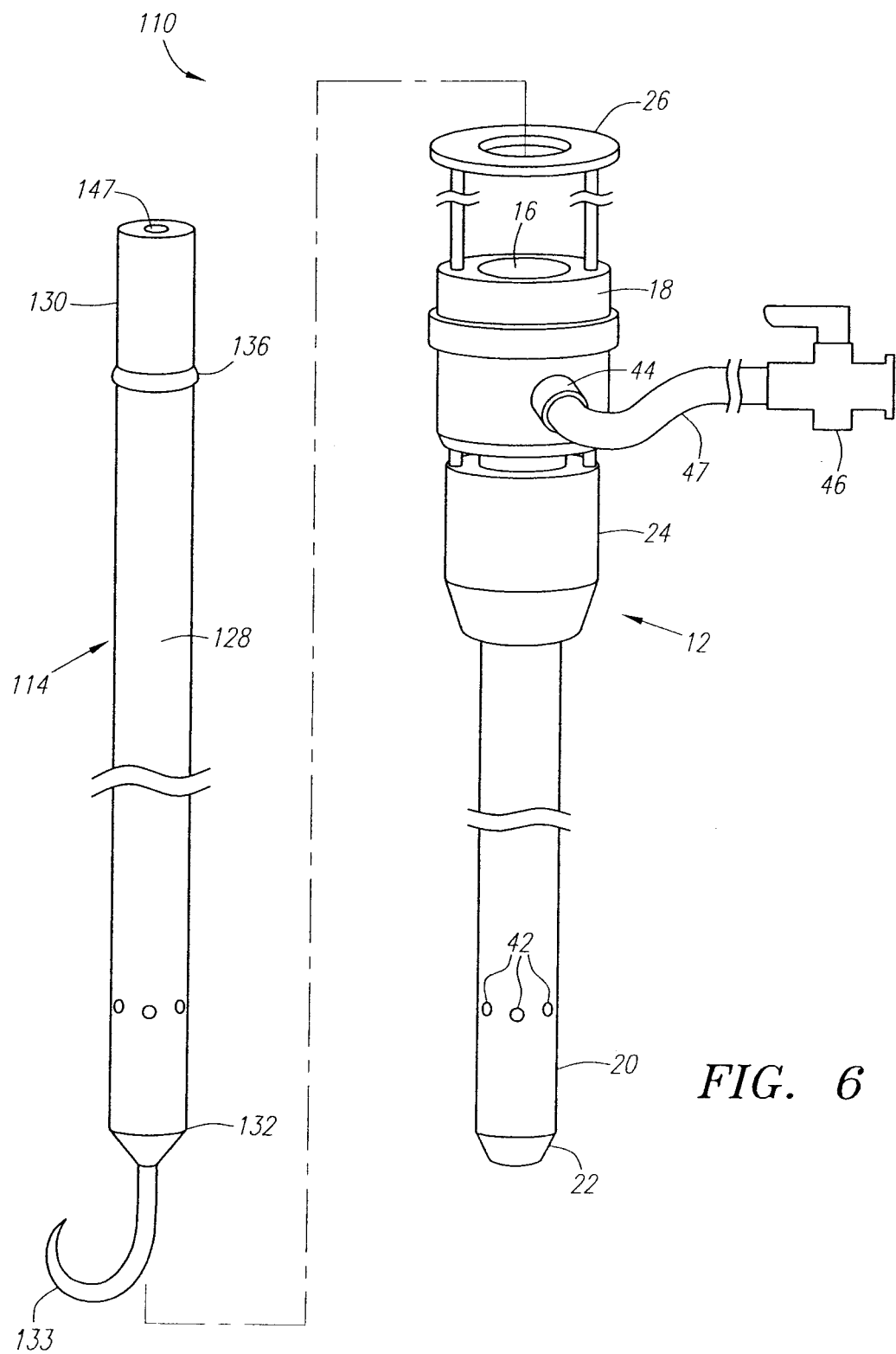
FIG. 6 is a side view of a second preferred embodiment of a vascular sheath and obturator, in accordance with the present invention.

As shown in FIG. 5, the sheath 12 and obturator 14 may then be advanced until the distal side ports 42 enter the blood vessel 90. Internal blood pressure within the blood vessel 90, which is substantially greater than the pressure encountered at the flush port 46, causes blood to enter the distal side ports 42, pass through the annular region 48, and exit the proximal side port 44. The flush port 46 may include substantially transparent tubing 47 such that the blood may be seen or a transparent cannula, chamber or other device may be connected to the flush port 46. Thus, the blood provides a visual indication that the sheath 12 and obturator 14 are properly positioned with respect to the wall 98 of the blood vessel 90.

With the sheath 12 properly positioned, the housing 24 may then be actuated, for example, to advance the housing 24 distally into the incision 92 to deliver the closure element (not shown). Preferably, the housing 24 may only be advanced a predetermined distance such that the closure device substantially engages the wall 98 of the blood vessel around the incision 92, e.g., until the barbs thereon penetrate but do not pass completely through the wall 98. Thus, the distal side ports 42 may be provided a predetermined distance from the distal end 18 of the sheath 12 and the housing 24 may be advanced only a predetermined distance, thereby providing a predetermined distance therebetween that may facilitate proper deployment of the closure element with respect to the wall 98 of the vessel 90.

Figure 7:
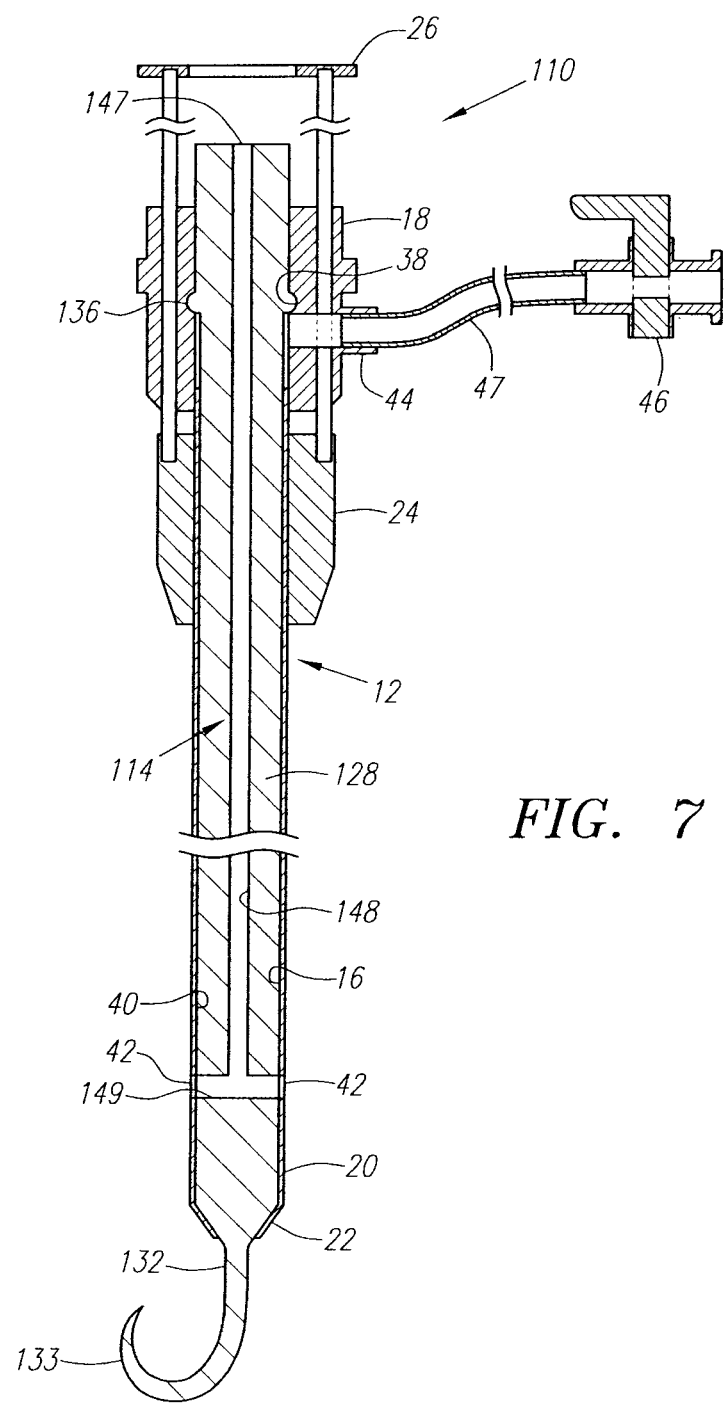
FIG. 7 is a cross-sectional view of the obturator and vascular sheath of FIG. 6, with the obturator fully inserted into the vascular sheath.

Turning to FIGS. 6-9, another preferred embodiment of an apparatus 110 is shown that includes a sheath 12 that is substantially identical to the previous embodiment, and an obturator 114. The obturator 114 is a substantially flexible, or semi-rigid elongate body 128 slidably engageable within a lumen 16 of the sheath 12 and having a proximal end 130 and a distal end 132. An annular ridge 136 is provided on the proximal end 130 that may engage a complementary-shaped pocket 38 or other cooperating detent in the sheath 12 for substantially securing the obturator 114 when it is fully inserted into the sheath 12. The distal end 132 of the obturator 114 may include a substantially flexible pigtail 133 that may facilitate atraumatic advancement into a blood vessel. As best seen in FIG. 7, the obturator 114 also includes a lumen 148 that extends from a proximal outlet 147 to an annular distal recess 149.

Figure 8:
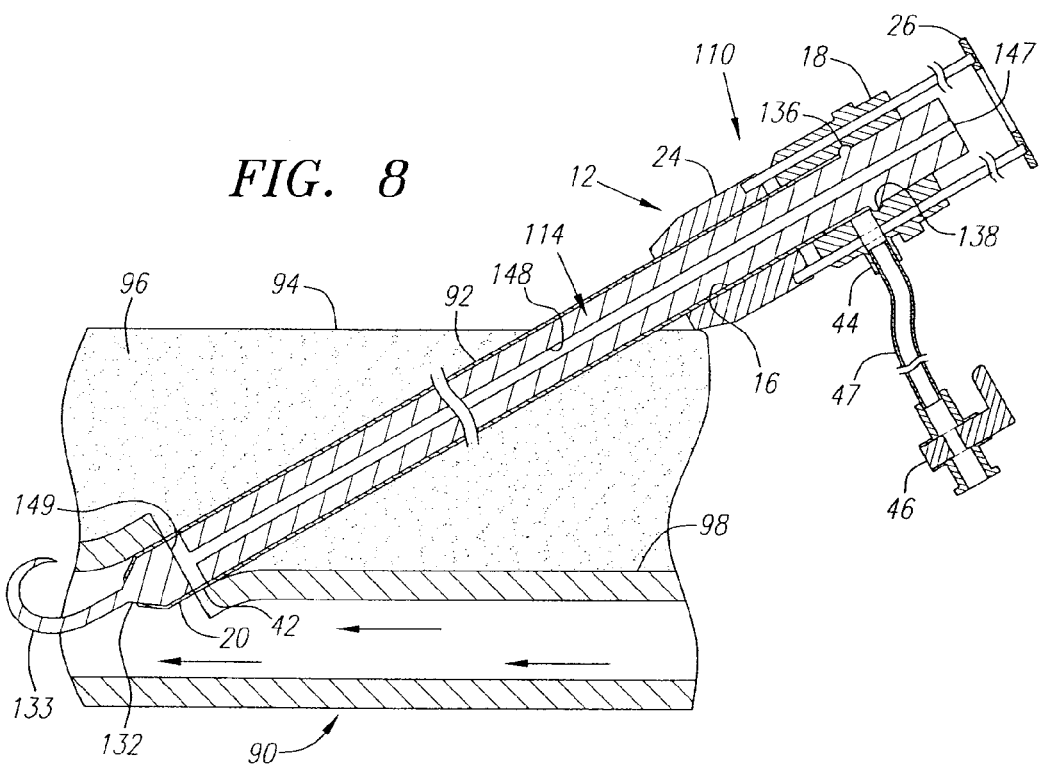
FIG. 8 is a cross-sectional view of the vascular sheath and obturator of FIG. 6 inserted through an incision into a blood vessel, showing side ports in the vascular sheath being disposed outside the blood vessel.

Turning to FIG. 8, the sheath 12 may be positioned within a blood vessel 90 through an incision 92 such that the distal side ports 42 do not communicate with an interior of the vessel 90. After one or more devices (not shown) are inserted through the sheath 12 to perform a desired procedure, the obturator 114 may be inserted into the lumen 16 until the distal end 132 extends beyond the distal end 20 of the sheath 12 and/or the cooperating detents 136, 38 are engaged. Preferably, when the obturator 114 is fully received within the sheath 12, the distal side ports 42 communicate with the annular recess 149. The sheath 12 and obturator 114 may then be moved in conjunction with one another, and preferably are together positioned such that the distal side ports 42 are adjacent to and not within the vessel 90.

Figure 9:
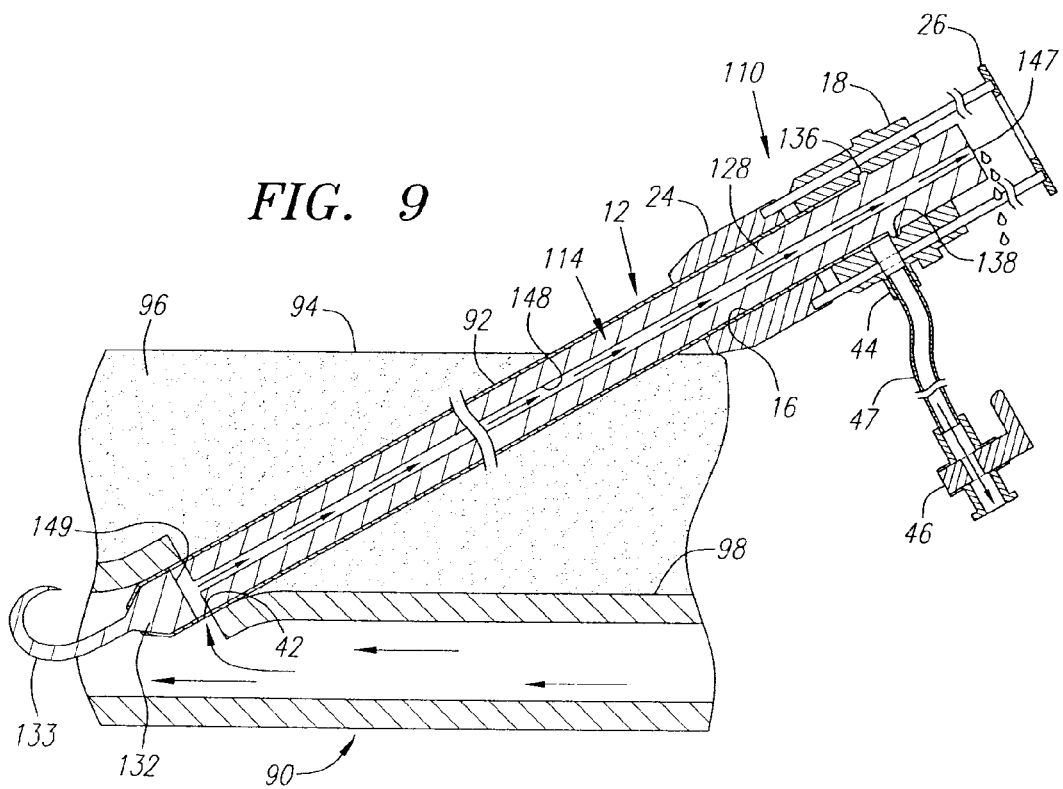
FIG. 9 is a cross-sectional view of the vascular sheath and obturator of FIG. 6 with the sheath advanced such that the side ports are disposed inside the blood vessel.
Figure 10:
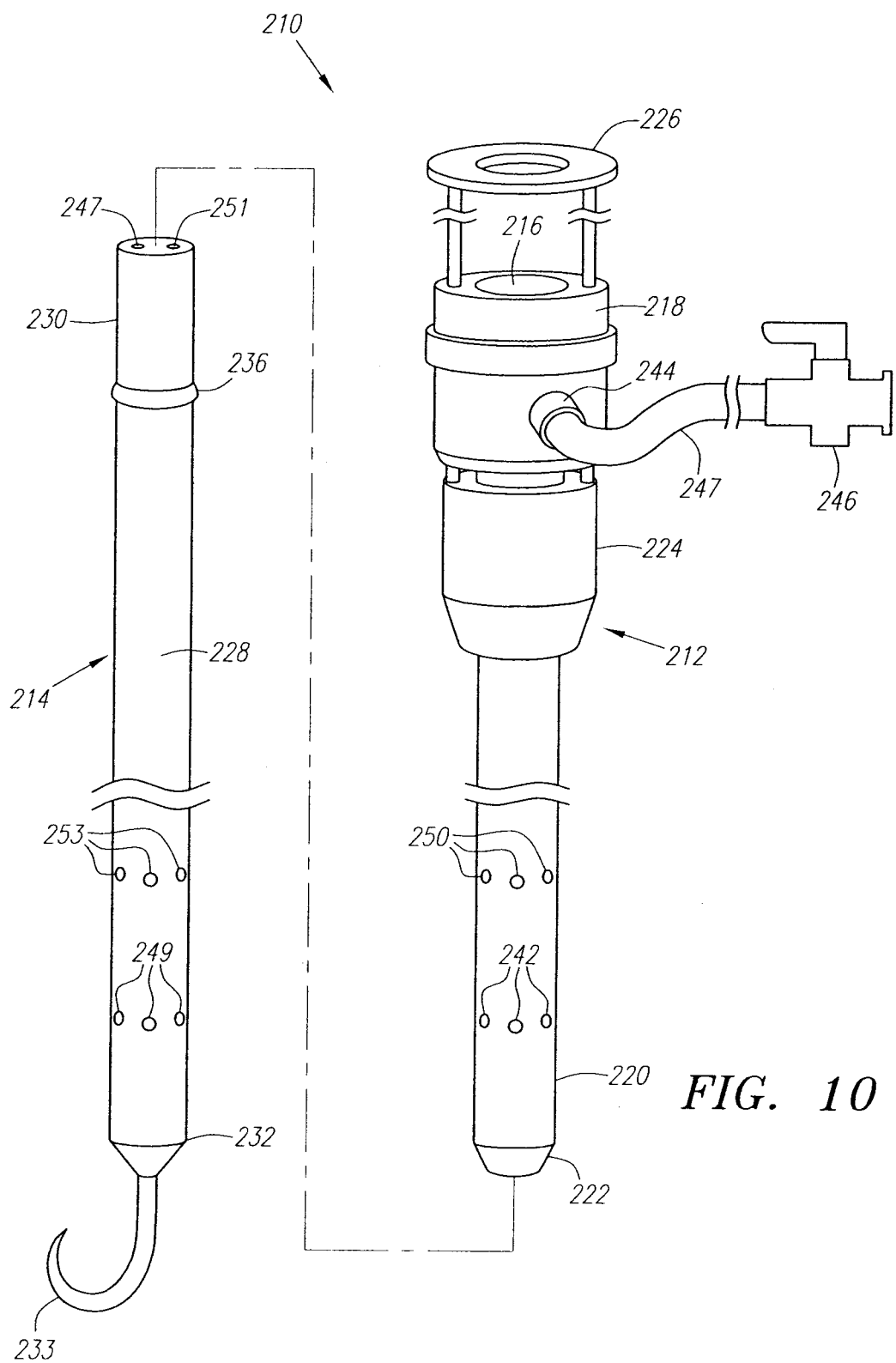
FIG. 10 is a side view of a third preferred embodiment of a vascular sheath and obturator, in accordance with the present invention.
Figure 11:
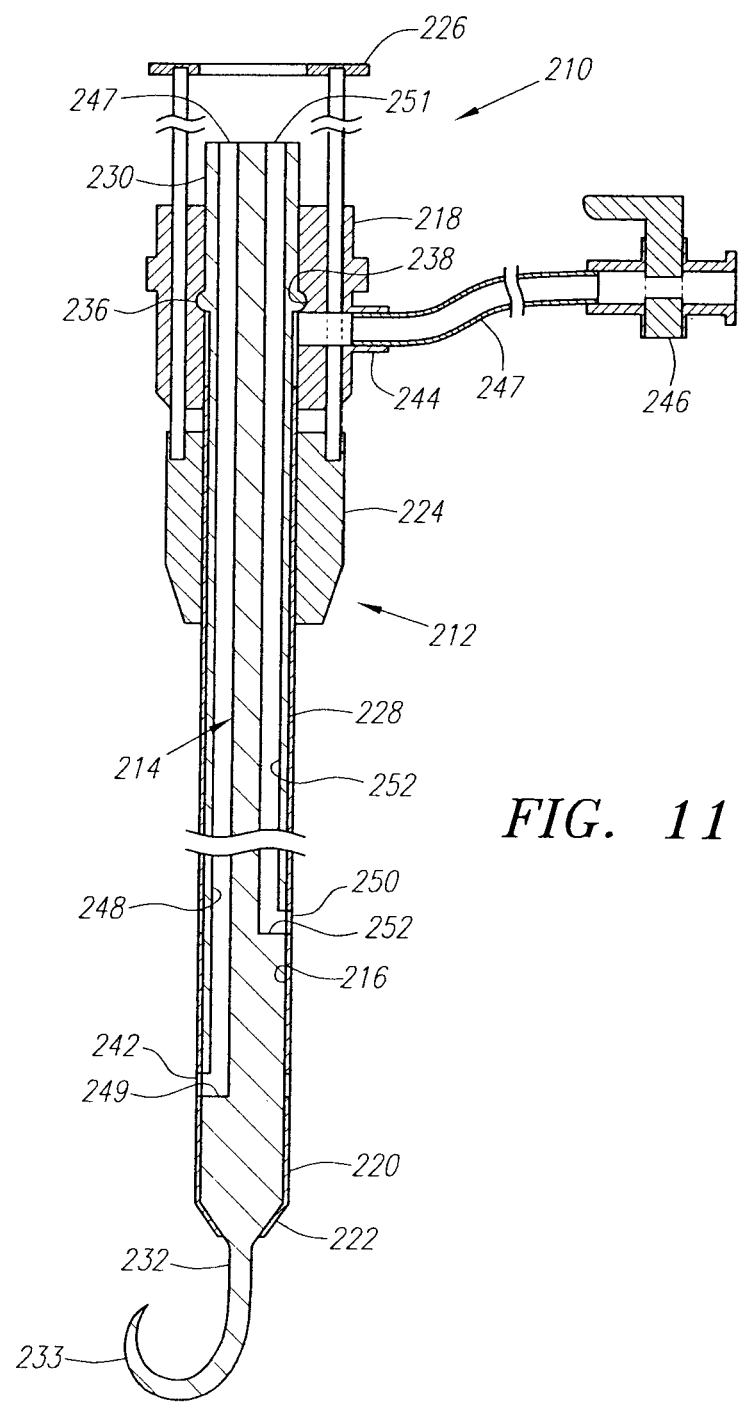
FIG. 11 is a cross-sectional view of the obturator and vascular sheath of FIG. 10, with the obturator fully inserted into the vascular sheath.

As shown in FIG. 9, the sheath 12 and obturator 114 may then be advanced until the distal side ports 42 enter the blood vessel 90. Internal blood pressure within the blood vessel 90 causes blood to enter the distal side ports 42 into the annular recess 149, pass through the lumen 148, and exit the proximal outlet 147. Thus, blood exiting the proximal outlet may provide a visual indication that the sheath 12 and obturator 114 are properly positioned with respect to the wall 98 of the blood vessel 90. The housing 24 may then be actuated to deliver the closure element, as described above.

Turning to FIGS. 10-13, yet another preferred embodiment of an apparatus 210 is shown that includes a sheath 212, and an obturator 214 insertable into the sheath 212. The sheath 212 includes a lumen 216 extending between its proximal and distal ends 218, 220. A housing 224 may be slidably disposed on an exterior of the sheath 212, the housing 224 configured for releasably holding a closure element, as described above (not shown).

The sheath 212 includes first and second sets of side ports 242, 250, each set preferably including a plurality of side ports that communicate with the lumen 216. The distal side ports 242 may be disposed circumferentially about a predetermined location along a length of the sheath 212, e.g., at a predetermined axial location with respect to the housing 224. The sheath 12 may also include a proximal side port 244 at or near the proximal end 218 that also communicates with the lumen 216, to which flush port 246 is connected. The sheath 212 also may include a seal (not shown) within the lumen 216 at or near the proximal end 218 that provides a fluid-tight seal, yet accommodates insertion of the obturator 214 into the lumen 216 without fluid passing proximally from the sheath 212.

The obturator 214 is a substantially flexible, or semi-rigid elongate body 228 having a size for slidably, but sealingly engaging an inner wall 240 of the sheath 212, and including a proximal end 230 and a distal end 232. An annular ridge 236 is provided on the proximal end 230 that may engage a complementary-shaped pocket 238 in the sheath 212 for substantially securing the obturator 214 within the sheath 212, similar to the embodiments described above. The distal end 232 of the obturator 214 my also be substantially soft and/or flexible, possibly including a pigtail (not shown), to facilitate atraumatic advancement into a blood vessel.

The obturator 214 includes first and second lumens 248, 252 that include first and second sets of distal openings 249, 253 and proximal openings 247, 251. Preferably, when the obturator 214 is fully received in the sheath 212, e.g., when the cooperating detents 236, 238 engage one another, the first and second sets of distal openings 249, 253 are axially aligned with the first and second sets of side ports 242, 250, respectively. The obturator 214 may be rotatable within the sheath 212 to further line the openings 249, 253 and side ports 242, 250 such that the first and second sets of side ports 242, 250 may communicate with the lumens 248, 252, respectively.

Figure 12:
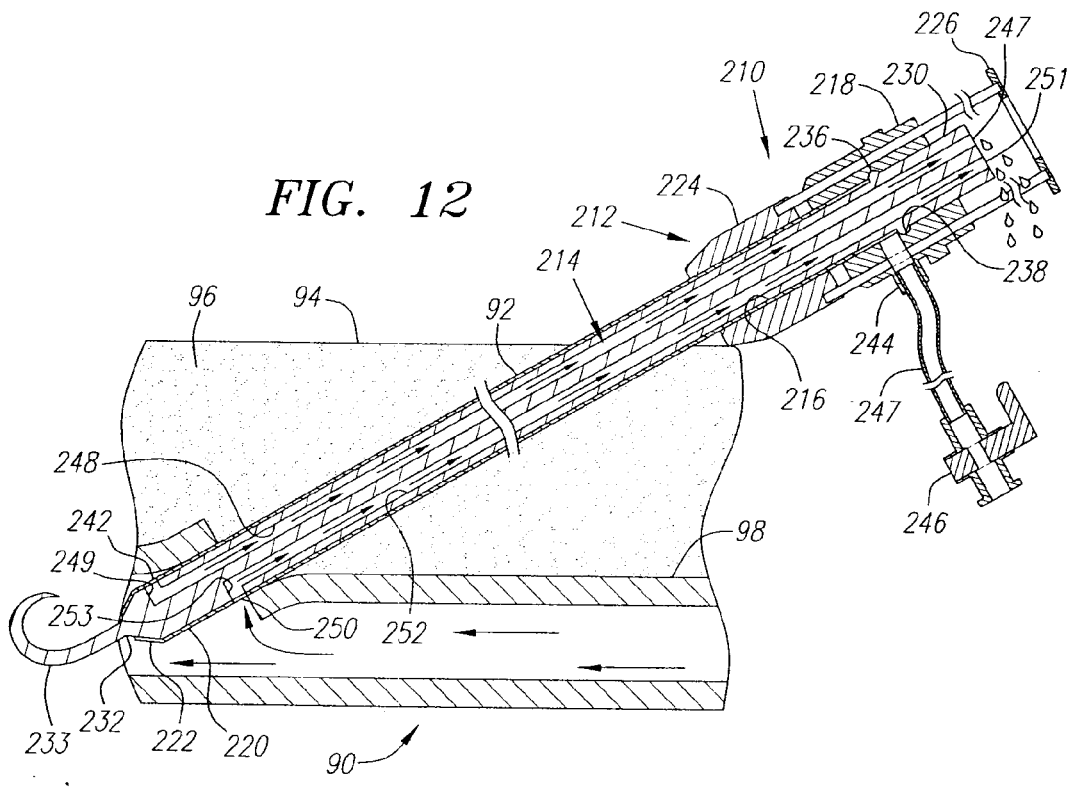
FIGS. 12 and 13 are cross-sectional views of the vascular sheath and obturator of FIG. 10 with the sheath advanced such that first and second backbleed ports in the vascular sheath are disposed within the blood vessel, and only first backbleed ports in the vascular sheath are disposed within the blood vessel, respectively.
Figure 13:
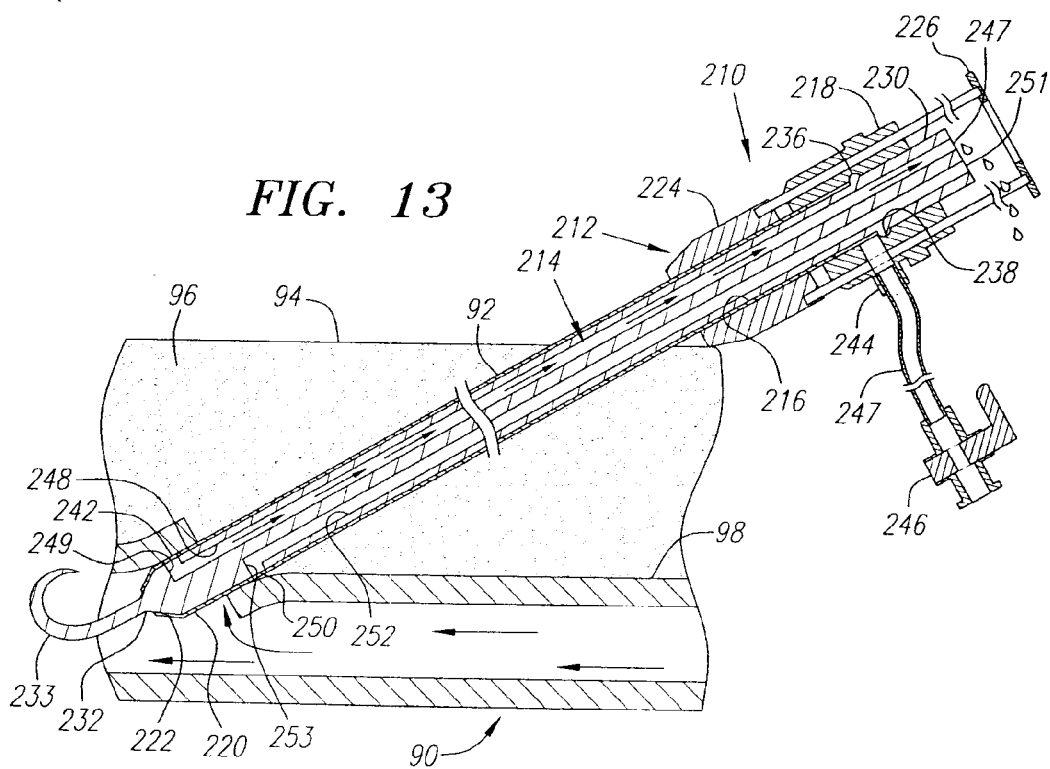

As best seen in FIGS. 12 and 13, during use of the apparatus 210, the sheath 212 may be disposed within a blood vessel 90 through an incision 92. After a procedure is completed using instruments introduced through the sheath 212, the obturator 214 may be inserted into the lumen 216 until the cooperating detents 236, 238 are engaged. If necessary, the obturator 214 may be rotated to align the first and second sets of side ports 242, 250 with the first and second sets of openings 249, 253, respectively. Alternatively, mating notches (not shown) may be provided, for example, on the cooperating detents 236, 238, that ensure that the obturator 214 and sheath 212 are rotatably aligned with one another.

The sheath 212 and obturator 214 may then be moved axially together into or out of the vessel 90. As shown in FIG. 12, in one position, both sets of side ports 242, 250 are exposed within the vessel 90, and the blood pressure therein, whereupon both proximal outlets 247, 251 may provide a "backbleed" visual indication. Alternatively, as shown in FIG. 13, only the distal or first set of side ports 242 may be exposed within the vessel 90, and provide a visual indication that the sheath 212 is not inserted as far as into the vessel 90 as in FIG. 12. In a further alternative, neither set of side ports 242, 250 may be provide a visual indication, indicating that the sheath 212 is withdrawn further or perhaps completely from the vessel 90.

Thus, a plurality of side ports at different axial positions along the sheath 212 may be used as a depth gauge, providing the user a visual indication that the sheath 212 is at one of a plurality of known locations or depths with respect to the vessel 90.

With the sheath 212 inserted a desired depth, the housing 224 may then be actuated to deliver the closure element (not shown). Alternatively, the housing and closure element may be eliminated, and the sheath 212 and obturator 214 may be used as an introducer device having a depth gauge indicator, as will be appreciated by those skilled in the art.

Figure 14A:
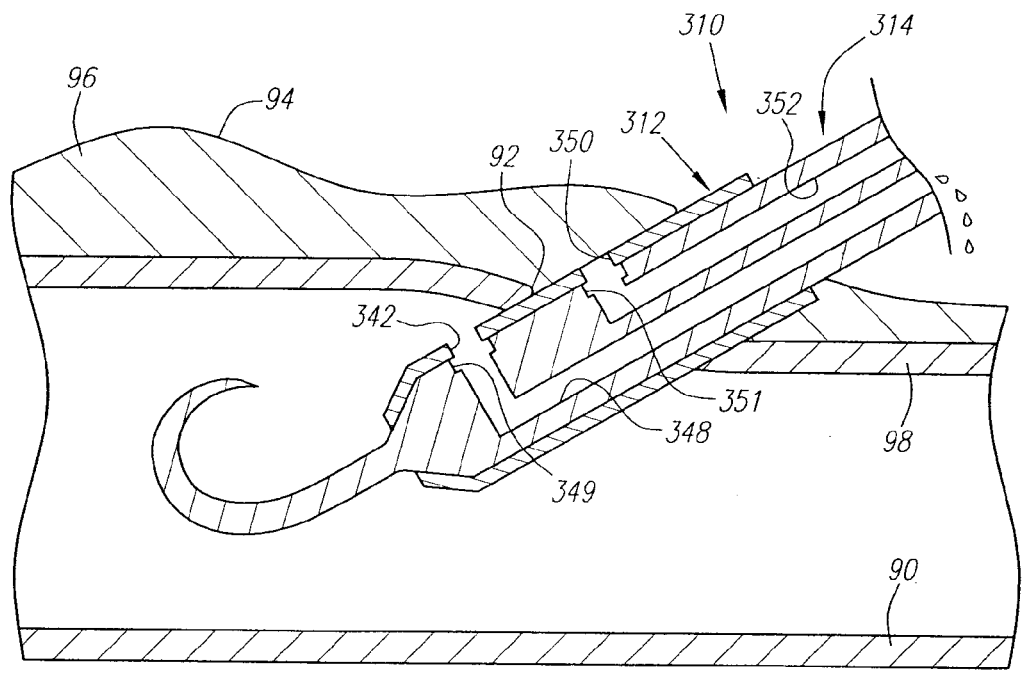
FIGS. 14A and 14B are cross-sectional views of a blood vessel, showing another preferred embodiment of a vascular sheath and obturator, including a pair of axially aligned backbleed ports in the vascular sheath.
Figure 14B:
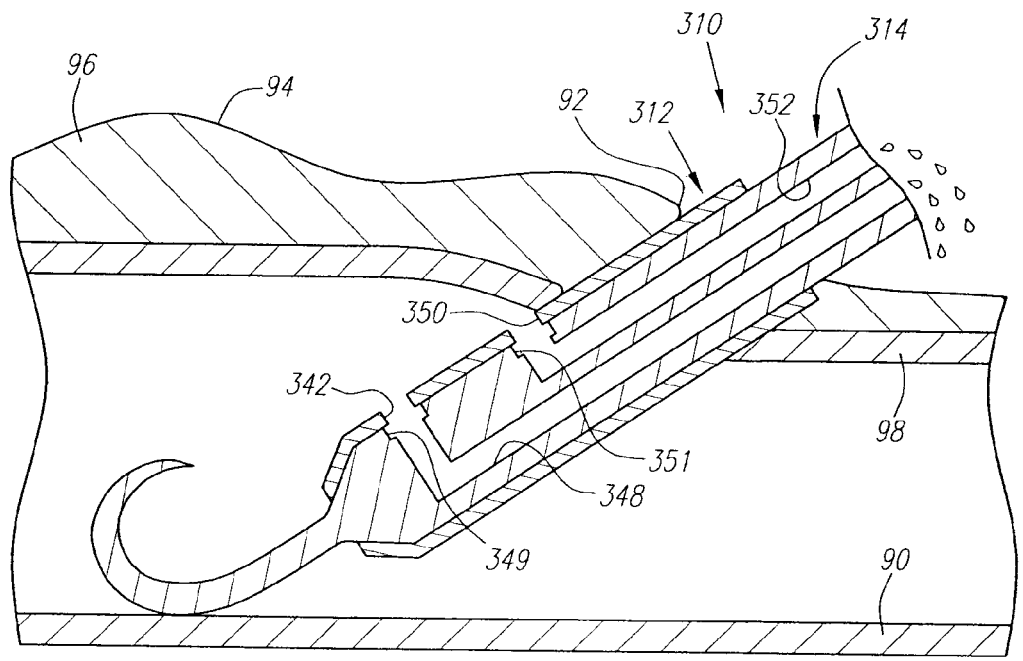

Turning to FIGS. 14A and 14B, still another preferred embodiment of an apparatus 310 is shown that includes a sheath 312 and obturator 314 similar to the previous embodiment. Unlike the previous embodiment, however, the sheath 312 includes first side port 342 and a second side port 350 instead of a plurality of side ports in each set. The first and second side ports 342, 350 are axially aligned with one another, i.e., at a similar peripheral location about the exterior of the sheath 312. The obturator 314 includes first and second annular recesses 349, 351 that are spaced apart axially a distance similar to the distance between the first and second side ports 342, 350. Thus, when the obturator 314 is fully inserted into the sheath 312, the first and second side ports 342, 350 are substantially aligned with the first and second annular recesses 349, 351, respectively, such that the first and second side ports 342, 250 communicate with first and second lumens 348, 352 within the obturator 314. In an alternative embodiment, the obturator may include a first lumen that may communicate with the first side port, and the obturator may include a reduced diameter region, similar to the embodiment shown in FIGS. 1 and 2, such that the second side port may communicate with the annular region defined between the sheath and the obturator.

The apparatus 310 preferably includes a visible marker (not shown), for example, on the proximal end (not shown) of the sheath 312 at a predetermined peripheral location. For example, the marker may be axially aligned with the first and second side ports 342, 350 to thereby provide a visual indication of the peripheral location of the side ports 342, 350. The apparatus 310 may then be used similar to the embodiments described above to position the sheath 312 within a blood vessel 90 and/or to deliver a closure element to close an incision 92 communicating with the vessel 90. During this procedure, the marker may be used to orient the sheath 312, for example, to rotate the side ports 342, 350 into an "anterior" orientation, i.e., towards the outer surface of the patient's skin 94. This may provide more precise control of the depth of the sheath, e.g., by taking into account the fact that the sheath 312 is inserted at an angle into the blood vessel 90, as will be appreciated by those skilled in the art.

Turning to FIGS. 15A and 15B, yet another embodiment of an apparatus 410 is shown that includes a sheath 412, and an obturator 414, similar to the previous embodiments. The apparatus 410 optionally may include a clip housing, clip, actuator handle and the like (not shown), e.g., on the sheath 412, similar to the previous embodiments. The sheath 412 includes first side port 442 and a second side port 450. The first and second side ports 442, 450 may be axially aligned with one another, i.e., at a similar peripheral location about the exterior of the sheath 412, or they may be offset from one another about the periphery. The obturator 414 includes an enlarged distal region 432, and a relatively narrow region 428 extending between the distal region 432 and a proximal end 430 of the obturator 414.

A protrusion 429, which may be a partial annulus or a hub, extends radially outward from the narrow region 428 to slidably engage an inner wall 440 of the sheath 412. The protrusion 429 is located a predetermined distance from the distal region 432 such that the protrusion 429 may selectively open or close the first and seconds side ports 442, 450. When the obturator 414 is inserted a first distance into the sheath 412, as shown in FIG. 15A, the protrusion 429 may sealably obstruct the second side port 450, thereby allowing fluid to enter the first side port 442 and pass through an annular lumen 448 to a proximal side port 444. The obturator 414 and sheath 412 may include cooperating detents, e.g., annular ridge 436 and a first annular groove 438a, for releasably securing the obturator 414 in the first position shown in FIG. 15A.

As shown in FIG. 15B, the obturator 414 may be advanced distally to a second position at which the protrusion 429 sealably obstructs the first side port 442, thereby allowing fluid to enter the second side port 450. The sheath 412 may include a second annular groove 438b for receiving the ridge 436 on the obturator 414 for releasably securing the obturator 414 in the second position.

During a procedure, the apparatus 410 may be used similar to the embodiments described above to position the sheath 412 within a blood vessel and/or to deliver a closure element to close an incision communicating with the vessel. First, the sheath 412 may be manipulated, e.g., advanced further into the vessel or retracted partially from the vessel, until the first and second side ports 442, 450 are positioned outside the vessel, i.e., within the puncture passage. A marker (not shown) may be used to orient the sheath 412, for example, to rotate the side ports 442, 450 into an "anterior" orientation, as described above. The obturator 414 may be inserted into the sheath 412 until it reaches the first position. The sheath 412 and obturator 414 may then be manipulated together, i.e., advanced or retracted, until internal blood pressure directs blood through the first side port 442 and into the proximal side port 444, indicating that the first side port 442 is within the vessel. The obturator 414 may then be advanced to the second position, occluding the first side port 442. The sheath 412 and obturator 414 may then be manipulated until blood enters the second side port 450 and exits the proximal side port 444, indicating the precise depth of the sheath 412.

Turning to FIGS. 16A and 16B, still another embodiment of an apparatus 510 is shown that includes a sheath 512, including first side port 542 and a second side port 550, and an obturator 514. The sheath 512 optionally may include a clip housing, clip, actuator handle and the like (not shown), similar to the previous embodiments. The first and second side ports 542, 550 may be axially aligned with one another, i.e., at a similar peripheral location about the exterior of the sheath 512, or they may be offset from one another about the periphery. The obturator 514 includes an enlarged distal region 532, and a relatively narrow region 528 extending between the distal region 532 and a proximal end 530 of the obturator 514.

An annular piston 529 extends radially outward from the narrow region 528 to slidably engage an inner wall 540 of the sheath 512, thereby sealing a region distal of the piston 529, i.e., between the piston 529 and the enlarged distal region 532. The piston 529 is located a predetermined distance from the distal region 528 such that the piston 529 may selectively open or close the first and seconds side ports 542, 550. The obturator 514 also includes a lumen 552 that extends from a proximal outlet 553 to a distal inlet 551 located distally of the piston 529.

When the obturator 514 is inserted a first distance into the sheath 512, as shown in FIG. 16A, the piston 529 may sealably obstruct the second side port 550, thereby allowing fluid to enter the first side port 542 and pass through the obturator lumen 552 to the proximal outlet 553. The obturator 514 and sheath 512 may include cooperating detents, e.g., annular ridge 536 and a first annular groove 538a, for releasably securing the obturator 514 in the first position shown in FIG. 16A.

As shown in FIG. 16B, the obturator 514 may be advanced distally to a second position at which the piston 529 sealably obstructs the first side port 550, thereby allowing fluid to enter the second side port 542 and pass through the annular lumen 548 to proximal side port 544. The sheath 512 may include a second annular groove 538b for receiving the ridge 536 on the obturator 514 for releasably securing the obturator 514 in the second position.

The apparatus 510 may be used similar to the embodiments described above to position the sheath 512 within a blood vessel and/or to deliver a closure element to close an incision communicating with the vessel. A marker (not shown) may be used to orient the sheath 512, for example, to rotate the side ports 542, 550 into an "anterior" orientation, as described above. The obturator 514 may be inserted into the sheath 512 until it reaches the first position. The sheath 512 and obturator 514 may then be manipulated, i.e., advanced or retracted, until internal blood pressure directs blood through the first side port 542 and into the proximal side port 544, indicating that the first side port 542 is within the vessel. The obturator 514 may then be advanced to the second position, occluding the first side port 550. The sheath 512 and obturator 514 may then be manipulated until blood enters the second side port 542 and exits the proximal side port 544, indicating the precise depth of the sheath 512.

Turning to FIGS. 17A-17H, yet another alternative embodiment is shown of an apparatus 610, including a sheath 612, including first and second side ports 642, 650, and an obturator 614. The sheath 612 optionally may include a clip housing, clip, actuator handle and the like (not shown), similar to the previous embodiments. The first and second side ports 642, 650 may be axially aligned with one another, i.e., at a similar peripheral location about the exterior of the sheath 612, as shown or they may be offset from one another about the periphery (not shown). The obturator 614 includes an enlarged distal region 632 that slidably and sealingly engages an inner wall 640 of the sheath 612. The obturator 614 also includes a relatively narrow region 628 extending between the distal region 632 and a proximal end 630 of the obturator 514, thereby defining an annular lumen 648 between the narrow region 628 and an inner wall 640 of the sheath 612.

A notch or slot 629 is provided in the distal region 632 of the obturator 614 that communicates with the lumen 648. The obturator 514 also includes a lumen 652 that extends from a proximal outlet 653 to a distal inlet 651 located distally of the notch 629. Preferably, the outlet 651 and the notch 629 are aligned with the first and second side ports 642, 650 when the obturator 614 is fully inserted into sheath 612.

The obturator 614 is rotatable within the sheath 612 between first and second positions. As best seen in FIGS. 17A and 17E, in the first position, the outlet 651 communicates with the first side port 642, while the second side port 650 is substantially sealed by the enlarged distal portion 632 of the obturator 614. Thus, fluid may enter the first side port 642 and pass through the obturator lumen 652 to the proximal outlet 653. The obturator 614 and sheath 612 may include cooperating detents 636, 638a for releasably securing the obturator 614 in the first position, as best seen in FIG. 17C.

As best seen in FIGS. 17B and 17G, the obturator 614 may be rotated to the second position such that the enlarged distal region 632 of the obturator 614 sealably obstructs the first side port 650, while fluid may freely enter the second side port 642 and pass through the notch 629 into the annular lumen 648 to proximal side port 644. The sheath 612 may include a second detent 638b for engaging the detent 636 on the obturator 614 for releasably securing the obturator 614 in the second position.

The apparatus 510 may be used similar to the embodiments described above to position the sheath 512 within a blood vessel and/or to deliver a closure element to close an incision communicating with the vessel, except that the obturator 614 is rotated within the sheath 612 rather than moved axially in order to selectively open or close the first and second side ports 642, 650. In an alternative embodiment, the obturator 614 may include two lumens (not shown), one that may selectively communicate with the respective first and second side ports 642, 650 when the obturator 614 is rotated within the sheath 612, as will be appreciated by those skilled in the art.

Figure 18:
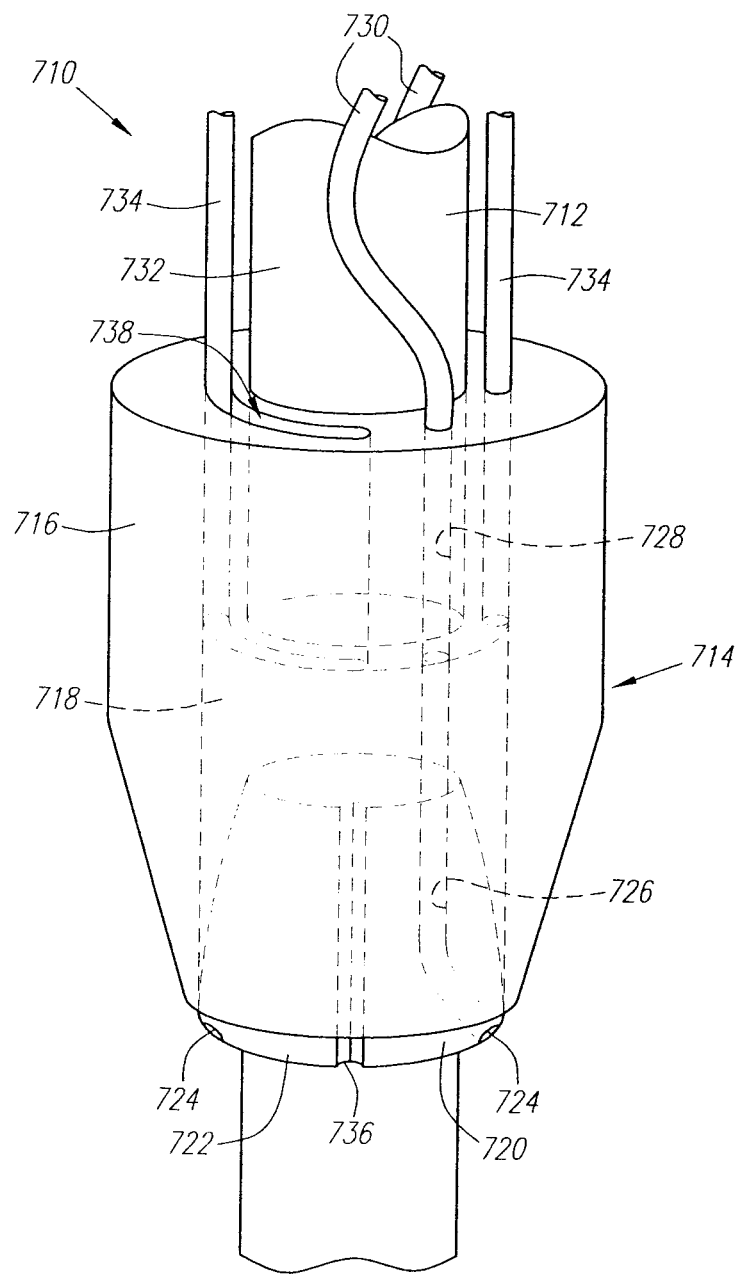
FIG. 18 is a detail of a clip housing on an introducer sheath, in accordance with the present invention.

Turning to FIG. 18, another embodiment of the present invention is shown, namely an apparatus 710 that includes a sheath or introducer 712, and a clip housing 714. The clip housing 714 includes an outer member 716 defining an annular cavity 718, and an inner member 720 that is partially receivable in the cavity 718. The inner member 720 includes a tapered distal end 722 within which are one or more ports 724. The ports communicate through a lumen 726 within the inner member 720 to a lumen 728 within the outer member 716 and to tubes 730. The clip housing 714 is slidable along an outer surface 732 of the sheath 712, and may be actuable, for example, using handle rods 734.

With the outer and inner members 716, 720 separated from one another, a clip or other closure device (not shown) may be placed within the cavity 718. For example, the inner member 720 may be removed distally from the sheath 712, and a clip may be advanced over the distal end (not shown) of the sheath 712 and into the cavity 718. The inner member 720 may then be advanced over the distal end of the sheath 712 until it partially enters the cavity 716, i.e., substantially engages the outer member 716. For example, the inner and outer members 720, 716 may include a cooperating groove 736 and notch (not shown) that may facilitate alignment and/or engagement of the inner and outer members 720, 716.

The sheath 712, with the clip housing 714 adjacent a proximal end thereof (not shown) may be placed through a puncture into a blood vessel, for example, until the distal end of the sheath 712 is disposed within the vessel lumen (not shown). A procedure may be completed, e.g., by introducing one or more instruments or other devices through the sheath 712 into the vessel. Upon completion of the procedure, the clip housing 714 may be advanced towards the distal end of the sheath 712, i.e., through the puncture until the clip housing just enters the vessel. The tapered end 722 of the inner member 720 may facilitate substantially atraumatic advancement of the clip housing 714 through the puncture with minimal harm to the surrounding tissue.

As the tapered end 722 enters the vessel, the ports 724 may communicate with the lumen, thereby causing blood to enter the ports, travel through the lumens 726, 728 and the tubes 730, thereby providing an indicator that the clip housing 714 has been properly positioned within the puncture. The clip housing 714 may then be activated, e.g., by rotating the rods 734 within slots 738, to deploy the clip. The sheath 712 may then be withdrawn from the vessel and puncture site, leaving the clip in the puncture site to substantially close the puncture opening into the vessel.

Figure 19A:
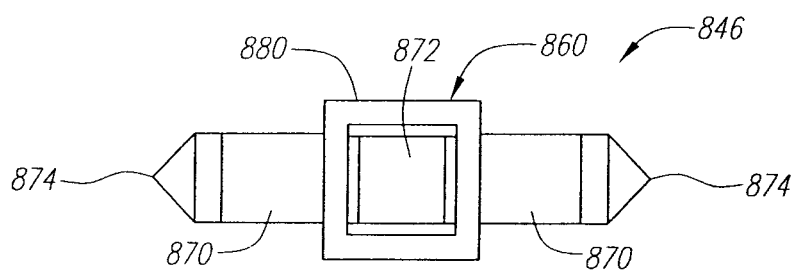
FIGS. 19A-19C are, respectively, views of a bioabsorbable clip and fastener of the present invention shown in top view in a delivery configuration, in side view in the delivery configuration, and in side view in a deployed configuration.
Figures 19B, 19C:
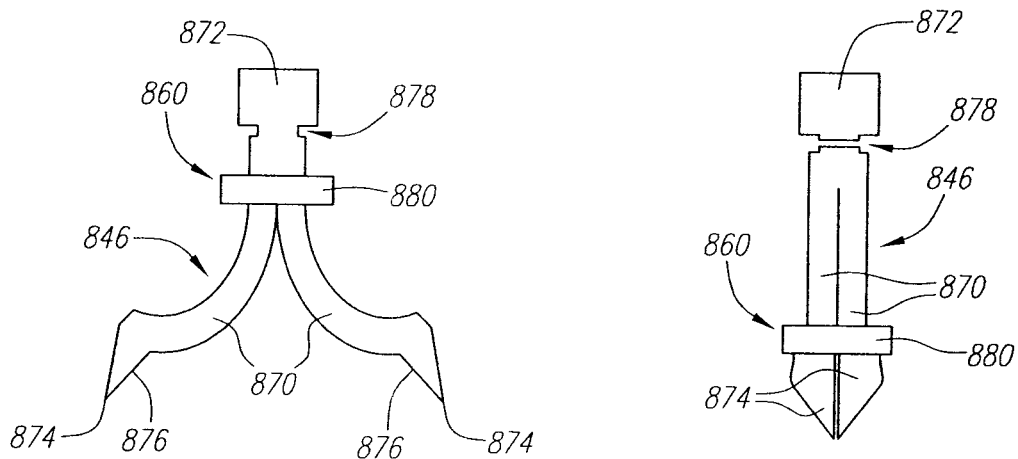

With reference now to FIGS. 19A-19C, bioabsorbable clip 846 and fastener 860 are described in greater detail. FIG. 19A shows clip 846 in the delivery configuration. Clip 846 comprises curved legs 870 and proximal end 872. Legs 870 distally terminate at spikes 874 with optional engagement means 876, and proximally terminate at narrowed region 878. Engagement means 876 may comprise, for example, barbs or hooks.

Fastener 860 comprises bioabsorbable locking collar 880, which is slidably received on the exterior of clip 846. As seen in FIG. 19B, locking collar 880 may be distally advanced down the exterior of clip 846 to deform the clip to its deployed configuration, wherein curved legs 870 and spikes 874 are drawn together. Clip 846 may then be separated from clip holder 856 by rotating proximal end 872 with respect to legs 870, causing the clip to snap into two pieces at narrowed region 878, for the reasons described hereinafter. Clip 846 and locking collar 880 preferably are fabricated from bioabsorbable materials, such as polyglycolic acid.

Figures 20A, 20B:
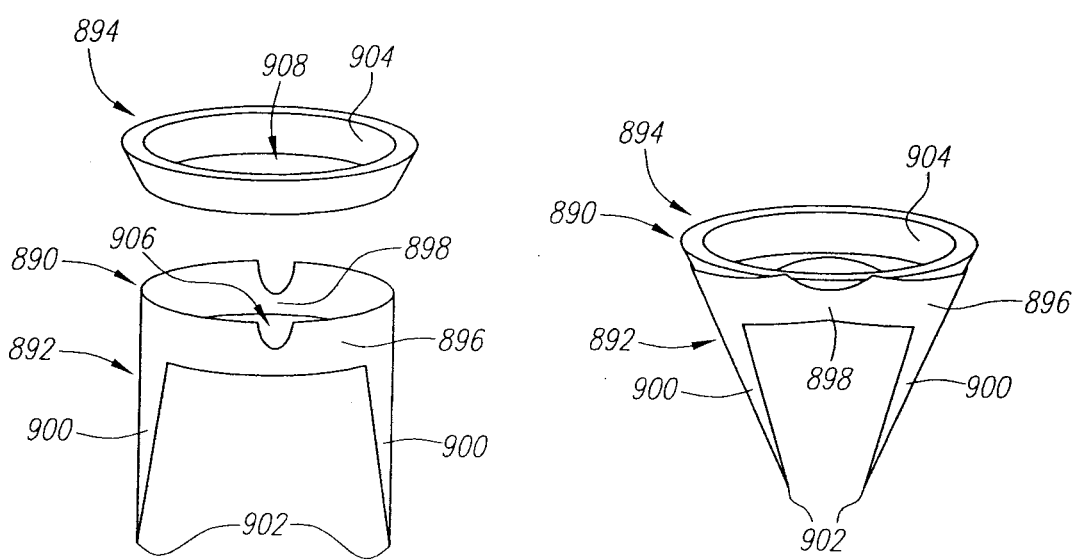
FIGS. 20A and 20B are isometric views of an alternative embodiment of the bioabsorbable surgical clip and fastener, constructed in accordance with the present invention and shown, respectively, in a delivery configuration and in a deployed configuration.

Referring to FIG. 20, an alternative embodiment of the closure component of the present invention is described. Closure component 890 comprises bioabsorbable clip 892 and fastener 894. Clip 892 comprises proximal hoop 896 with narrowed regions 898, and legs 900 terminating in spikes 902. Fastener 894 comprises bioabsorbable wedge 904. Wedge 904 has a diameter substantially equal to the diameter of hoop 896 at its distal end, the diameter tapering to a maximum diameter at the proximal end of wedge 904. Clip 892 therefore may be deformed from the delivery configuration of FIG. 20A to the deployed configuration of FIG. 20B, wherein legs 900 and spikes 902 are drawn together, by advancing wedge 904 into hoop 896 to deform clip 892 at narrowed regions 898. Lumen 906 extends through hoop 898 of clip 892, while lumen 908 extends through wedge 896. Clip 892 and wedge 896 therefore are configured for delivery over the exterior of an introducer sheath. The clip and wedge preferably are fabricated from bioabsorbable materials.

With reference to FIGS. 21A-21B through 24A-24B, in conjunction with FIGS. 1-3, methods of using vascular device 10 are described. Introducer sheath 12 is advanced through skin, fat, and muscle tissue into vessel V, through vascular puncture P, which is formed in accordance with well-known techniques. Vascular device 10 is used in the same manner as a standard introducer sheath.

As shown in FIG. 21A, distal pins 850, mounted in housing 816, abut distal slots 866 and 868 of drivers 858 and holders 856, respectively.

FIG. 21B illustrates closure component 820 via sectional views. FIG. 21A shows the locations of proximal pins 854 within proximal slots 862 and 864, and the locations of distal pins 850 within distal slots 866 and 868, corresponding to the relative longitudinal positions of clip holders 856 and locking collar drivers 858 depicted in FIG. 21B. Pin locations are shown via side views of clip holders 856 and locking collar drivers 858 at the relevant locations.

As seen in FIGS. 21A and 21B, with clip housing 816 positioned at puncture site P, proximal pins 854, mounted in caps 852. are positioned at the extreme right of proximal driver slots 862 and of the circumferential portions of proximal holder slots 864. Distal pins 850 are located at the distal end of distal driver slots 866 and of the longitudinal portions of distal holder slots 868.

In FIGS. 22A and 22B, with clip housing 816 held immobile, force is applied to caps 852 to distally advance clips 846 with respect to housing 816. Specifically, proximal pins 854 abut and apply force against proximal slots 862 and 864, which advances drivers 858 and clip holders 856, as well as attached clips 846 and locking collars 880. Distal pins 850 move freely within distal slots 866 and the longitudinal portions of distal slots 868. Distal advancement of clips 846 continues until pins 850 abut against the proximal end of the longitudinal portions of distal holder slots 868 of clip holders 856. Drivers 858 likewise are restrained by their connection to clip holders 856 via proximal pins 854. The tissue-engaging members, spikes 874 and engagement means 876, of clips 846 contact and pierce the wall of vessel V on opposite sides of the puncture site P.

As seen in FIGS. 23A and 23B, once the spikes have pierced the vessel wall, locking collar drivers 858 are advanced distally while clip housing 816 and clip holders 856 remain stationary, thereby distally advancing locking collars 880 down the exteriors of clips 846 to draw legs 870 and spikes 874 together to close puncture P. Engagement means 876 serve to retain the clips within the vessel wall during healing.

To achieve this advancement of drivers 858 with respect to clip holders 856, caps 852 are rotated clockwise, as viewed from above, until proximal pins 854 abut against the extreme left of proximal slots 862 and 864, thereby aligning the pins with the longitudinal portions of proximal holder slots 864. Then, force is once again applied to caps 852 to advance drivers 858 and deform clips 846 to their deployed configurations. Specifically, proximal pins 854 abut and apply force to proximal driver slots 862, thereby distally advancing drivers 858. Pins 854 move freely within the longitudinal portions of proximal holder slots 864 until they abut against the distal ends of slots 864. Likewise, distal driver slots 866 move freely until distal pins 850 abut the proximal ends of slots 866. In FIG. 23A, when proximal pins 854 abut slots 864 and distal pins 850 abut slots 866, locking collars 880 have been driven down the exteriors of clips 846, thereby deforming the clips to draw legs 870 together and close the puncture site.

In FIGS. 24A and 24B, with clips 846 deformed to seal puncture P, clip holders 856 are detached from clips 846 by snapping the clips free at narrowed regions 878. At this point, or prior to detachment, a suitable biocompatible bioglue or tissue sealant optionally may be injected into the puncture tract, as discussed hereinabove, through device port 832 or side port 822, to aid in sealing vascular puncture P. Alternatively, the bioglue or tissue sealant may be delivered through the backbleed path described above. Vascular device 10 then is withdrawn from the vessel wall, completing the procedure.

Clips 846 are detached from clip holders 856 by rotating caps 852 counterclockwise, as viewed from above. Proximal pins 854 of caps 852 move freely within proximal driver slots 862, but abut against the distal end of the longitudinal portions of proximal holder slots 864 and cause clip holders 856 to rotate with respect to collar drivers 858. Distal pins 850 of clip housing 816 move freely within the circumferential portions of distal holder slots 868 during rotation of clip holders

856. Meanwhile, drivers 858 are restrained from rotation by distal pins 850, which abut against distal driver slots 866. Bioabsorbable clips 846 do not rotate because the square cross section of square clip bores 847 of drivers 858 matches the substantially square cross section of clips 846, thus, since drivers 858 are restrained from rotation, so are clips 846. Non-square cross sections for clips 846 and bores 847, capable of performing the restraining function, will be apparent to those of skill in the art and fall within the scope of the present invention.

Since clips 846 are restrained while clip holders 856 rotate, and since proximal ends 872 of clips 846 are attached to clip holders 856, counterclockwise rotation of caps 852 causes clips 846 to snap at their weakest points: narrowed regions 878. Vascular device 10 may then be removed from the patient to complete the procedure.

Although preferred illustrative embodiments of the present invention are described above, it will be evident to one skilled in the art that various changes and modifications may be made without departing from the invention. For example, with minor modifications, vascular device 10 may be configured to carry closure component 890 of FIG. 20, or any of a variety of alternative bioabsorbable and deformable clips. Proximal pins 854 may be formed integrally with caps 852, and distal pins 850 may be formed integrally with clip housing 816. Any number of clips 846 may be used to close the vascular puncture.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for accurately positioning a sheath in order to deliver a vascular closure element into engagement with a puncture site in a blood vessel, the apparatus comprising:
   a sheath having a proximal end that terminates in a proximal opening, an external side port at or near the proximal end for providing visual confirmation of bleed back, a distal end that terminates in a distal opening, a lumen extending between the proximal and distal openings formed by a wall of the sheath, and a plurality of ports in fluid communication with the lumen and disposed at a location on the sheath to be used for positioning the sheath in relation to the puncture site of the blood vessel;
   a housing slidably cooperating with the sheath, the housing releasably holding a vascular closure element and being slidably actuable to move the vascular closure element into position to engage with tissue adjacent the puncture site of the blood vessel; and
   an elongate member insertable into the lumen of the sheath, the elongate member comprising a distal end of the elongate member that contacts the wall of the sheath to seal the lumen to prevent blood from entering the lumen from the distal opening but does not obscure the plurality of ports so that blood can continue to enter the plurality of ports in order to flow through the lumen and exit the external side port, to provide visual confirmation of bleed back, indicating that the sheath is correctly positioned in relation to the puncture site of the blood vessel to permit correct deployment of the vascular closure element, the distal end of the elongate member contacting the wall of the sheath and sealing the lumen of the sheath and also being distal the distal end of the sheath as the housing slidably cooperates with the sheath to move the vascular closure element, the vascular closure element including tines configured to pierce the blood vessel.

2. The apparatus as recited in claim 1, wherein the distal end is at least partially tapered.

3. The apparatus as recited in claim 2, wherein the distal region further comprises a flexible pigtail.

4. The apparatus as recited in claim 1, wherein the elongate member further comprises a lumen extending from the distal end toward a proximal region, the lumen being in fluid cooperation with the plurality of ports.

5. An apparatus for accurately positioning a sheath in order to deliver a vascular closure element into engagement with a puncture site in a blood vessel:
   a sheath having a proximal end that terminates in a proximal opening, an external side port at or near the proximal end for providing visual confirmation of bleed back, a distal end that terminates in a distal opening, a lumen extending between the proximal and distal openings formed by a wall of the sheath, and a plurality of ports in fluid communication with the lumen and disposed at a location on the sheath to be used for positioning the sheath in relation to the puncture site of the blood vessel;
   a housing slidably cooperating with the sheath, the housing releasably holding a vascular closure element and being slidably actuable to move the vascular closure element into position to engage with tissue adjacent the puncture site of the blood vessel; and
   an elongate member insertable into the lumen of the sheath, the elongate member comprising a mechanism to secure the elongate member inside the sheath at a position where a distal end of the elongate member contacts the wall of the sheath to seal the lumen to prevent blood from entering the lumen from the distal opening but does not obscure the plurality of ports so that blood can continue to enter at least one of the plurality of ports in order to flow through the lumen and exit the external side port, to provide visual confirmation of bleed back, indicating that the sheath is correctly positioned in relation to the puncture site of the blood vessel to permit correct deployment of the vascular closure element, the distal end of the elongate member contacting the wall of the sheath and sealing the lumen of the sheath and also being distal the distal end of the sheath, and extending into the blood vessel, as the housing slidably cooperates with the sheath to move the vascular closure element, the vascular closure element including tines configured to pierce the blood vessel.

6. The apparatus as recited in claim 5, wherein the elongate member further comprises one or more annular recesses in fluid communication with the lumen.

7. The apparatus as recited in claim 5, wherein the elongate member further comprises a protrusion disposed proximal to the distal end, the protrusion selectively positionable within the first lumen to vary the fluid path.

8. The apparatus as recited in claim 7, wherein the protrusion is selectively positionable adjacent one or more of the one or more first ports to vary the fluid path.

9. The apparatus as recited in claim 5, wherein the elongate member further comprises a piston disposed proximal to the distal region, the piston selectively positionable within the first lumen to vary the fluid path.

10. The apparatus as recited in claim 5, wherein the housing further includes an outer member defining the annular cavity and an inner member partially receivable in the annular cavity.

11. The apparatus as recited in claim 10, wherein the inner member further includes a distal end with one or more second ports.

12. The apparatus as recited in claim 10, wherein the one or more second ports are in fluid communication with a second lumen in the inner member and a third lumen in the outer member.

13. An apparatus for accurately positioning a sheath in order to deliver a vascular closure element into engagement with a puncture site in a blood vessel, the apparatus comprising:
- a sheath having a proximal end that terminates in a proximal opening, an external side port at or near the proximal end for providing visual confirmation of bleed back, a distal end that terminates in a distal opening, a lumen extending between the proximal and distal openings formed by a wall of the sheath, and a plurality of ports in fluid communication with the lumen and disposed at a location on the sheath to be used for positioning the sheath in relation to the puncture site of the blood vessel;
- a housing slidably cooperating with the sheath, the housing releasably holding a vascular closure element and being slidably actuable to move the vascular closure element into position to engage with tissue adjacent the puncture site of the blood vessel; and
- an elongate member for insertion into the lumen of the sheath and for preventing blood from entering the lumen from the distal opening but not obscuring the plurality of ports so that blood can continue to enter at least one of the plurality of ports in order to flow through the lumen and exit the external side port, to provide visual confirmation of bleed back, indicating that the sheath is correctly positioned in relation to the puncture site of the blood vessel to permit correct deployment of the vascular closure element,
- wherein a cooperation of the elongate member and the sheath positions the distal end of the elongate member to contact the wall of the sheath and seal the lumen of the sheath, with a distal end of the elongate member being distal the distal end of the sheath and within the blood vessel, as the housing slidably cooperates with the sheath to move the vascular closure element, the vascular closure element including tines configured to pierce the blood vessel.

14. The apparatus as recited in claim 13, wherein the housing slidably cooperates with an exterior surface of the sheath.

15. The apparatus as recited in claim 13, wherein the elongate member further comprises a mechanism to secure the elongate member inside the sheath at a position where the distal end of the elongate member seals the lumen to prevent blood from entering the lumen from the distal opening but does not obscure the plurality of ports so that blood can continue to enter the at least one of the plurality of ports in order to flow through the lumen and exit the proximal side port, to indicate that the sheath is correctly positioned in relation to the puncture site of the blood vessel to permit correct deployment of the vascular closure element.

16. The apparatus as recited in claim 13, wherein the elongate member selectively translates relative to the sheath to vary the fluid path from the plurality of ports toward the distal end of the sheath.

17. The apparatus as recited in claim 13, wherein the elongate member selectively rotates relative to the sheath to vary the fluid path from the one or more ports toward the distal end of the sheath.

18. The apparatus as recited in claim 13, wherein the elongate member and the sheath selectively move in an anterior direction to position the plurality of ports in fluid communication with the lumen.

19. The apparatus as recited in claim 13, wherein the distal end is expandable to sealingly engage the portion of the first lumen.

20. The apparatus as recited in claim 13, wherein the vascular closure element comprises a biodegradable clip.

* * * * *